US008755505B2

(12) United States Patent
Sankai

(10) Patent No.: US 8,755,505 B2
(45) Date of Patent: Jun. 17, 2014

(54) COMMUNICATION WALL PANEL, NURSING CARE SYSTEM HAVING COMMUNICATION WALL PANEL, AND CONFERENCE SYSTEM HAVING COMMUNICATION WALL PANEL

(75) Inventor: Yoshiyuki Sankai, Ibaraki (JP)

(73) Assignee: University of Tsukuba, Ibaraki (JP)

( * ) Notice: Subject to any disclaimer, the term of this patent is extended or adjusted under 35 U.S.C. 154(b) by 426 days.

(21) Appl. No.: 13/122,465

(22) PCT Filed: Oct. 27, 2009

(86) PCT No.: PCT/JP2009/068413
§ 371 (c)(1),
(2), (4) Date: Apr. 4, 2011

(87) PCT Pub. No.: WO2010/050474
PCT Pub. Date: May 6, 2010

(65) Prior Publication Data
US 2011/0187812 A1    Aug. 4, 2011

(30) Foreign Application Priority Data

Oct. 28, 2008    (JP) ................................ 2008-276738

(51) Int. Cl.
*H04M 3/42*    (2006.01)
*H04M 1/00*    (2006.01)
*H04M 9/00*    (2006.01)

(52) U.S. Cl.
USPC .............. 379/201.1; 379/201.01; 379/428.01; 379/435; 379/443; 379/444

(58) Field of Classification Search
USPC ................ 379/90.01, 93.01, 93.21, 157, 158, 379/201.01, 202.01, 207.01; 348/14.01, 348/14.02, 14.03, 14.04, 14.05, 14.06, 14, 348/7, 14.08, 14.09, 14.1, 14.11, 14.12, 348/14.13, 14.14, 15.15, 14.16; 370/259, 370/260, 261, 262; 455/414.1, 416
See application file for complete search history.

(56) References Cited

U.S. PATENT DOCUMENTS 6,014,432 A * 1/2000 Modney .................... 379/106.02
7,283,153 B2 * 10/2007 Provost et al. ............. 348/14.01
(Continued)

FOREIGN PATENT DOCUMENTS

| JP | 3-252258 | 11/1991 |
|---|---|---|
| JP | 9-288456 | 11/1997 |

(Continued)

OTHER PUBLICATIONS

International Search Report mailed on Nov. 24, 2009.

(Continued)

*Primary Examiner* — Khai N Nguyen
(74) *Attorney, Agent, or Firm* — IPUSA, PLLC

(57) ABSTRACT

A communication wall panel includes an interior panel member to be attached to a room as an interior wall material thereof; an information obtaining part provided in the interior panel member and configured to obtain information associated with a person in the room; a notification part provided in the interior panel member and configured to notify the person in the room of information; a communication part provided in the interior panel member and configured to perform communication with a server installed in a location other than the room; and a control part provided in the interior panel member and configured to control the information obtaining part and the notification part. The communication part is configured to transmit information obtained from the information obtaining part to the server and to output information transmitted from the server to the notification part.

5 Claims, 19 Drawing Sheets

(56) References Cited

U.S. PATENT DOCUMENTS

| | | | |
|---|---|---|---|
| 2007/0118831 A1* | 5/2007 | Kondo | 717/121 |
| 2007/0179646 A1* | 8/2007 | Dempski et al. | 700/83 |
| 2008/0015900 A1* | 1/2008 | Denholm | 705/2 |
| 2008/0068447 A1* | 3/2008 | Mattila et al. | 348/14.08 |
| 2008/0106374 A1* | 5/2008 | Sharbaugh | 340/5.8 |
| 2009/0001082 A1* | 1/2009 | Goldenne et al. | 220/477 |
| 2009/0027483 A1 | 1/2009 | Sakai | |
| 2009/0237487 A1* | 9/2009 | Santini | 348/14.01 |

FOREIGN PATENT DOCUMENTS

| | | |
|---|---|---|
| JP | 10-224756 | 8/1998 |
| JP | 2000-050249 | 2/2000 |
| JP | 2003-004863 | 1/2003 |
| JP | 2006-303997 | 11/2006 |

OTHER PUBLICATIONS

Japanese Office Action mailed Aug. 7, 2012.

* cited by examiner

COMMUNICATION WALL PANEL, NURSING CARE SYSTEM HAVING COMMUNICATION WALL PANEL, AND CONFERENCE SYSTEM HAVING COMMUNICATION WALL PANEL

TECHNICAL FIELD

The present invention relates to a communication wall panel having multiple functions, a nursing care system having the communication wall panel, and a conference system having the communication wall panel.

BACKGROUND ART

For example, in the case of a care recipient who lives with home-visit nursing care services at home, the care recipient communicates with a home-visit nursing care company that provides the home-visit nursing care services, a care manager who manages the home-visit nursing care services, rehabilitation facilities, a hospital, and a nursing care taxi company to have a nursing care service plan prepared so that the nursing care services are provided according to the planned schedule.

There is a support system for supporting such home/home-visit nursing care, where a video camera, a microphone, and a display unit, as well as a communications unit for transmitting an image signal captured by the video camera and an audio signal detected with the microphone to a center and receiving an image signal and an audio signal transmitted from the center and a control unit to control apparatuses, are set up in a care recipient's room so as to connect the care recipient's room and a server on the center side in a communicable manner. (See, for example, Patent Document 1 listed below.)

Further, there is a videoconference system for videoconferencing through the Internet by multiple conference participants at distant locations, where a camera, a microphone, a loudspeaker, a display unit, a communications unit for transmitting and receiving an image signal and an audio signal, and a control unit to control apparatuses are disposed in the room of each conference participant so as to transmit an image signal and an audio signal to a conference server through a communication line and receive an image signal and an audio signal from another conference participant. (See, for example, Patent Document 2 listed below.)

PRIOR ART DOCUMENTS

Patent Document

[Patent Document 1] Japanese Laid-Open Patent Application No. 10-224756
[Patent Document 2] Japanese Laid-Open Patent Application No. 2006-303997

SUMMARY OF THE INVENTION

Problems to be Solved by the Invention

According to the systems described in Patent Documents 1 and 2, in setting up apparatuses for transmitting and receiving image information and audio information (a camera, a microphone, a loudspeaker, a display unit, a communications unit, and a control unit) in the room of a care recipient or a conference participant, the apparatuses are provided individually. Accordingly, a lot of time and effort is required in a setup operation including placing the apparatuses on a desk and connecting the apparatuses with cables.

Further, a lot of cables are tangled on the backsides of the apparatuses, which not only looks ugly but also requires time and effort in performing checking at the time of failure occurrence, thus resulting in the problem of complicated maintenance work.

Means for Solving the Problems

According to an aspect of the present invention, an object of the present invention is to provide a communication wall panel, a nursing care system having the communication wall panel, and a conference system having the communication wall panel in which one or more of the above-described problems may be solved or reduced.

According to an aspect of the present invention, a communication wall panel includes an interior panel member to be attached to a room as an interior wall material thereof; an information obtaining part provided in the interior panel member and configured to obtain information associated with a person in the room; a notification part provided in the interior panel member and configured to notify the person in the room of information; a communication part provided in the interior panel member and configured to perform communication with a server installed in a location other than the room; and a control part provided in the interior panel member and configured to control the information obtaining part and the notification part, wherein the communication part is configured to transmit information obtained from the information obtaining part to the server and to output information transmitted from the server to the notification part.

According to an aspect of the present invention, a nursing care system includes an interior panel member to be attached to a room of a care recipient as an interior wall material of the room; an information obtaining part provided in the interior panel member and configured to obtain image information and audio information associated with the care recipient in the room; a notification part provided in the interior panel member and configured to notify the care recipient in the room of image information and audio information from outside the room; a communication part provided in the interior panel member and configured to perform communication; a control part provided in the interior panel member and configured to control the information obtaining part and the notification part; and a server configured to receive, from the communication part, the image information and the audio information associated with the care recipient obtained from the information obtaining part, and to transmit the received image information and the audio information associated with the care recipient to a terminal installed in a location separate from the room.

According to an aspect of the present invention, a conference system includes an interior panel member to be attached to a room of each of a plurality of conference participants as an interior wall material of the room; an information obtaining part provided in the interior panel member and configured to obtain image information and audio information associated with a first one of the conference participants in the room; a notification part provided in the interior panel member and configured to notify the first one of the conference participants in the room of image information and audio information associated with a second one of the conference participants; a communication part provided in the interior panel member and configured to perform communication; a control part provided in the interior panel member and configured to control the information obtaining part and the notification part; and a server configured to receive, from the communication part, the image information and the audio information associated with the first one of the conference participants obtained from the information obtaining part, and to transmit the image information and the audio information associated with the second one of the conference participants to the communication part.

Effects of the Invention

According to an aspect of the present invention, an information obtaining part, a notification part, a communication part, and a control part are provided in an interior panel member. Accordingly, it is possible to attach these apparatuses (parts) to a room in a single operation by attaching the interior panel member. This substantially reduces time and effort for installation work compared with the case of installing them individually, thus making it possible to perform installation with efficiency. Further, the work for interconnecting apparatuses is simplified, and it is possible to provide multiple cables without their exposure.

BRIEF DESCRIPTION OF THE DRAWINGS

Other objects, features and advantages of the present invention will become more apparent from the following detailed description when read in conjunction with the accompanying drawings, in which.

MODE FOR CARRYING OUT THE INVENTION

A description is given, with reference to the accompanying drawings, of an embodiment of the present invention.

Figure 1:
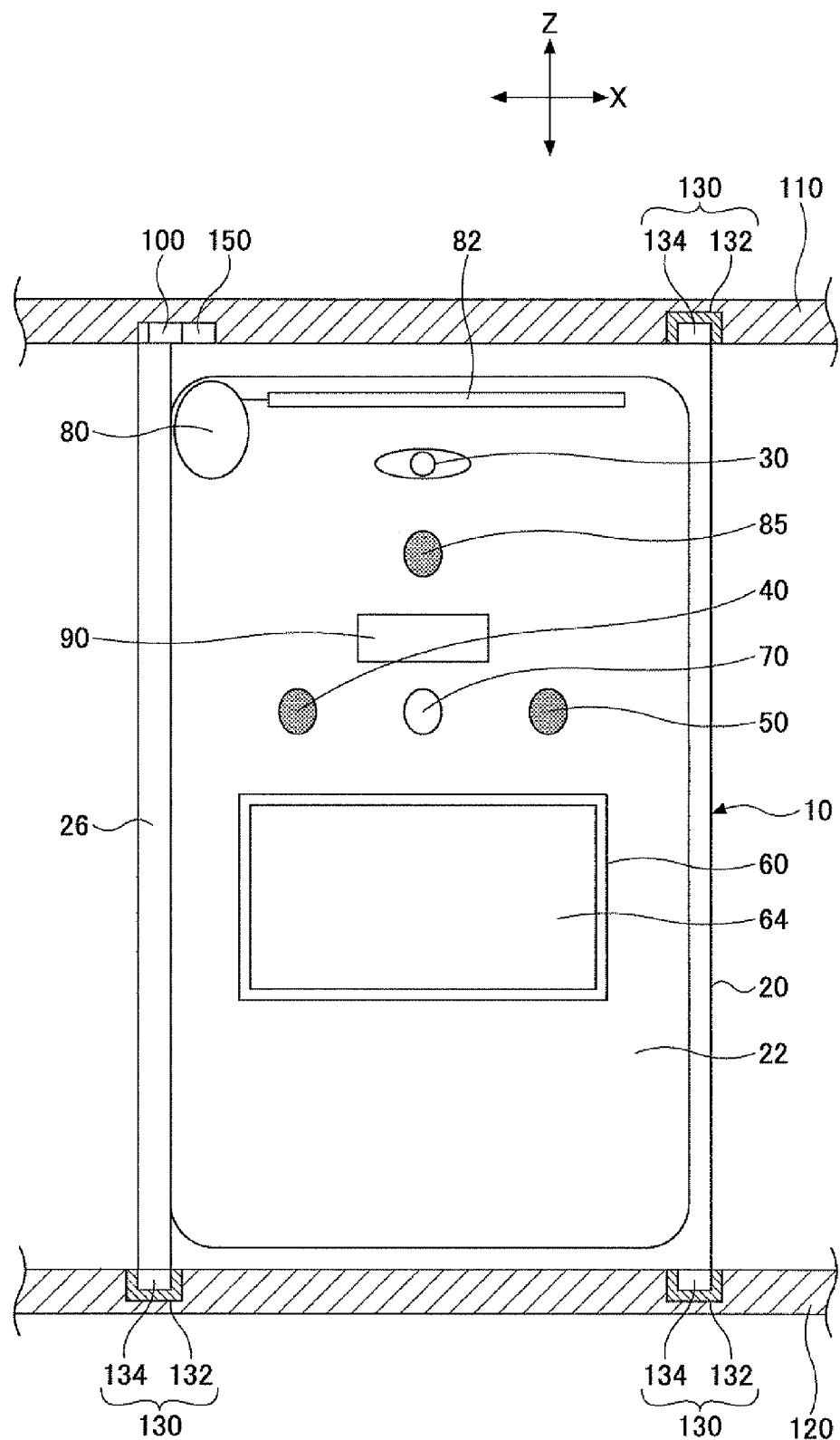
FIG. 1 is a diagram illustrating a communication wall panel according to an embodiment of the present invention.

FIG. 1 is a diagram illustrating a communication wall panel 10 according to the embodiment of the present invention.

Figure 2:
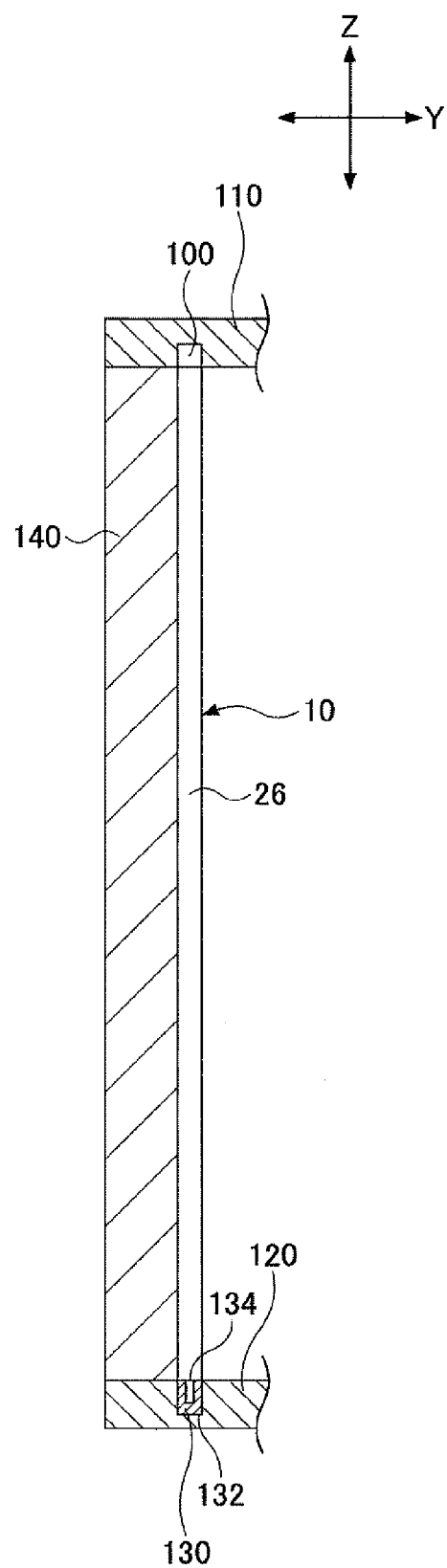
FIG. 2 is a side view of the communication wall panel, illustrating its attachment state, according to the embodiment of the present invention.

FIG. 2 is a side view of the communication wall panel 10, illustrating its attachment state.

Figure 3:
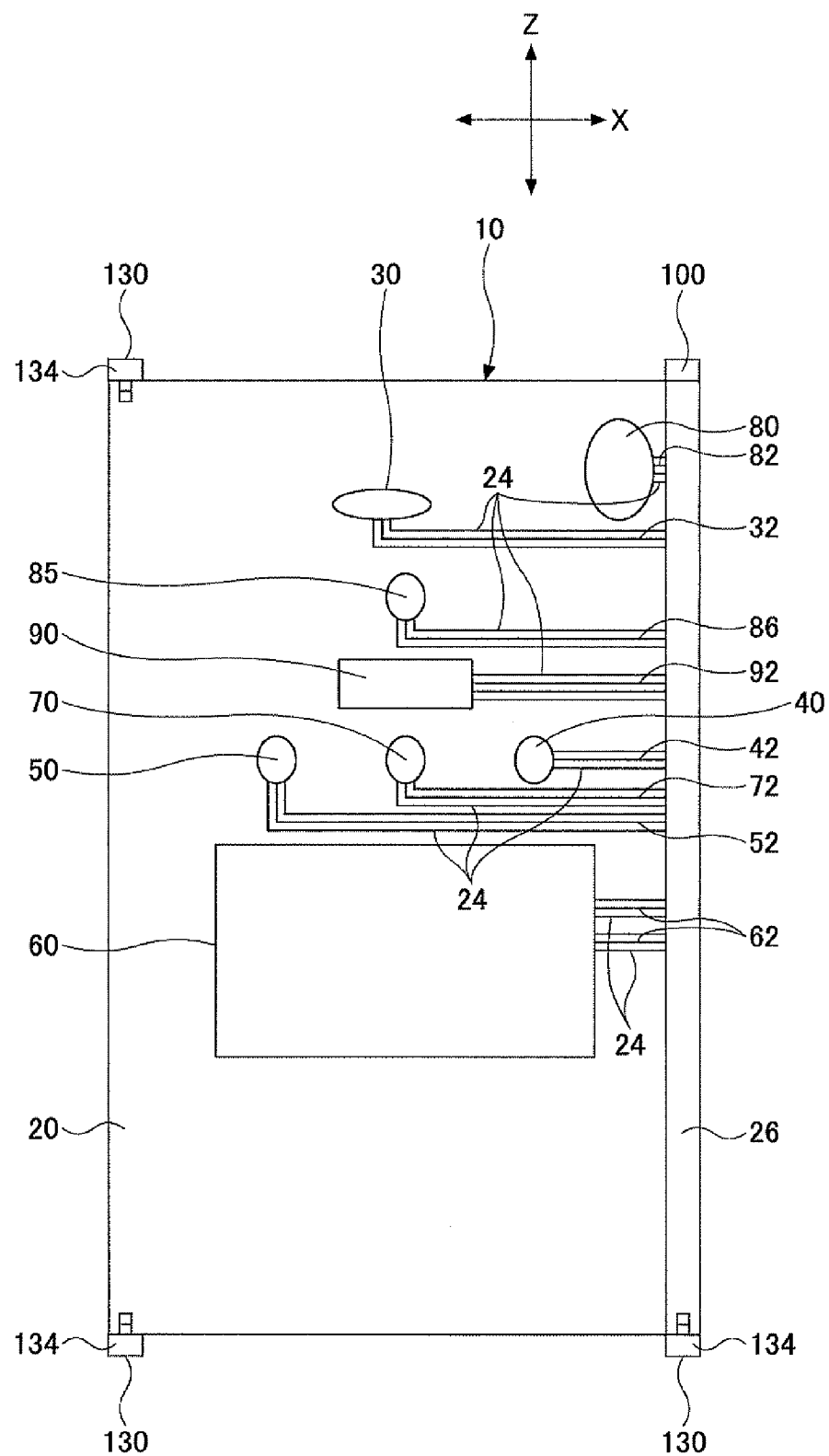
FIG. 3 is a rear view of the communication wall panel according to the embodiment of the present invention.

FIG. 3 is a rear view of the communication wall panel 10.

As illustrated in FIG. 1 through FIG. 3, the communication wall panel 10 includes an interior panel member 20; a digital video camera 30, a microphone 40, and a temperature sensor 50 to serve as an information obtaining part; a display unit 60 and a loudspeaker 70 to serve as a notification part; a communication modem 80 to serve as a communication part; an infrared communication module 85 to transmit a wireless signal using infrared based on a short range wireless communications standard (such as ZigBee); and a control unit 90 to serve as a control part. The digital video camera 30, the microphone 40, the temperature sensor 50, the display unit 60, the loudspeaker 70, the communication modem 80, the infrared communication module 85, and the control unit 90 are provided in the interior panel member 20. Further, the interior panel member 20 is formed of an interior material such as wood to have a panel shape. The face (front face) of the interior panel member 20 is covered with a decorative sheet 22 of a color matched with the interior wall paper or painting color of a room.

The digital video camera 30 is set up so as to take an image of the interior of the room as well as an image of a person in the room. Further, the digital video camera 30 has a zooming function to take an enlarged image of the face of a speaker in the case of using the communication wall panel 10 as an IP (Internet Protocol) telephone or a terminal unit for a videoconference. Further, the digital video camera 30 also operates as a monitoring camera to monitor a care recipient in the case of using the communication wall panel 10 in nursing care facilities or hospitals.

The microphone 40 operates as a sound detection part to detect sound in the room and a vibration detection part to detect vibration in the room. Further, the microphone 40 also operates as, for example, a telephone receiver to detect voice sound in the room and output a voice signal in the case of using the communication wall panel 10 as a television IP telephone or a terminal unit for a videoconference. Further, for example, monitoring a change in the level of a room sound detection signal output by the microphone 40 makes it possible to determine the presence or absence of an abnormality in a care recipient in the case of using the communication wall panel 10 in nursing care facilities or hospitals. For example, the microphone 40 detects an abnormal sound or a vibration when the care recipient tumbles in the room or detects the sound made by the fall of a piece of tableware from a table.

The temperature sensor 50 operates as a temperature detection part to detect the temperature of the room as well as a body temperature detection part to monitor the presence of a person in the room and the presence or absence of an abnormality in the body temperature of the person by detecting the body temperature of the person. Further, for example, the temperature sensor 50, which employs infrared thermography to image temperature distribution by detecting infrared rays in the room, detects a change in the temperature distribution of the room or in the body temperature of a person.

The display unit 60, which includes a flat-screen display such as a liquid crystal panel or an organic EL (electroluminescence) display, is provided in the substantial center of the front face of the interior panel member 20. Further, the display unit 60 is a display part to display image information transmitted from a server. The display unit 60, which has a touchscreen panel 64 on a screen, also operates as an input part through operations of the touchscreen panel 64.

The loudspeaker 70 is an audio output part to output audio information transmitted from a server, and also operates as a telephone receiver for listening to an audio signal transmitted from another party in the case of IP telephone or conducting a videoconference.

The communication modem 80 is a communication part to perform radio transmission and reception through a film-shaped antenna 82. For example, the communication modem 80 has such a communication board as is installed in cellular phones housed in a resin case. The communication modem 80 is used, for example, as a communication part for intra-building (for example, room-to-room) calls.

The infrared communication module 85 transmits, by infrared, such control signals as to turn on or off a home appliance (such as an air conditioner, a television, or a stereo) installed in the room based on the voice instruction of a person in the room, to change the set temperature of the air conditioner, to change the reception channel of the television, and to select a tune to be played on the stereo.

The control unit 90, which is a controller having semiconductor devices such as a central processing unit (CPU) 94 (FIG. 6) and a memory 96 (FIG. 6) mounted on a board, controls devices such as the digital video camera 30, the microphone 40, the temperature sensor 50, the display unit 60, the loudspeaker 70, the communication modem 80, and the infrared communication module 85. Further, control programs for executing control modes such as a room monitoring control mode, an IP telephone mode, and a videoconference control mode may be prestored in the control unit 90. The control unit 90 operates as a control part to execute specified control modes or control modes reserved for respective time periods at corresponding set times in order by selecting the specified or reserved control modes.

Devices such as the digital video camera 30, the microphone 40, the temperature sensor 50, the display unit 60, the loudspeaker 70, the communication modem 80, the infrared communication module 85, and the control unit 90 are attached to be housed in respective attachment recesses formed on the face (front face) of the interior panel member 20, and are accordingly prevented from projecting from the front surface of the interior panel member 20. Further, as illustrated in FIG. 3, cables 32, 42, 52, 62, 72, 82, 86, and 92 extended from the digital video camera 30, the microphone 40, the temperature sensor 50, the display unit 60, the loudspeaker 70, the communication modem 80, the infrared communication module 85, and the control unit 90, respectively, are provided on the back face (rear face) of the interior panel member 20. The cables 32, 42, 52, 62, 72, 82, 86, and 92 are housed in respective interconnection grooves 24 formed on the back face of the interior panel member 20 so as not to project from the back face.

Referring to FIG. 1, a vertically extending interconnection duct 26 is attached to the left side face of the interior panel member 20. The interconnection duct 26, which is formed of a resin material or an aluminum alloy material, has a hollow structure with a space for inserting the cables 32, 42, 52, 62, 72, 82, 86, and 92 through.

A connector member 100, to which the cables 32, 42, 52, 62, 72, 82, 86, and 92 inserted through the interconnection duct 26 are connected, is attached to the upper end of the interconnection duct 26 so as to be slidable horizontally (in the X directions). Since the connector member 100 is provided at the upper end of the interconnection duct 26, the connector member 100 is housed in a ceiling 110 so as not to be exposed in the room. The cables 32, 42, 52, 62, 72, 82, 86, and 92, which are provided on the back face (rear face) side of the interior panel member 20, do not hinder the installation of the communication wall panel 10. Further, since the cables 32, 42, 52, 62, 72, 82, 86, and 92 are provided in advance, there is no need to do wiring on site. This makes it possible to complete the installation work in a short period of time.

A fixation mechanism 130 for fixing the communication wall panel 10 to the ceiling 110 and a floor 120 is provided at the lower end of the interconnection duct 26 and at the upper right end and the lower right end of the interior panel member 20 in its front view (FIG. 1). The fixation mechanism 130 includes an engagement member 132 embedded in the ceiling 110 and the floor 120 and a stopper member 134 to engage or be disengaged from the engagement member 132. The stopper member 134 is provided so as to be movable vertically (in the Z directions), so that the stopper member 134 is easily movable to an engagement position or a disengagement position. Accordingly, the communication wall panel 10 is fixed to the ceiling 110 and the floor 120 with the fixation mechanism 130 at three points.

The information obtaining part, which is formed of the digital video camera 30, the microphone 40, and the temperature sensor 50 according to this embodiment, may be formed of at least one of the digital video camera 30, the microphone 40, and the temperature sensor 50. Further, the notification part, which is formed of the display unit 60 and the loudspeaker 70 according to this embodiment, may be formed of at least one of the display unit 60 and the loudspeaker 70.

Figure 4A:
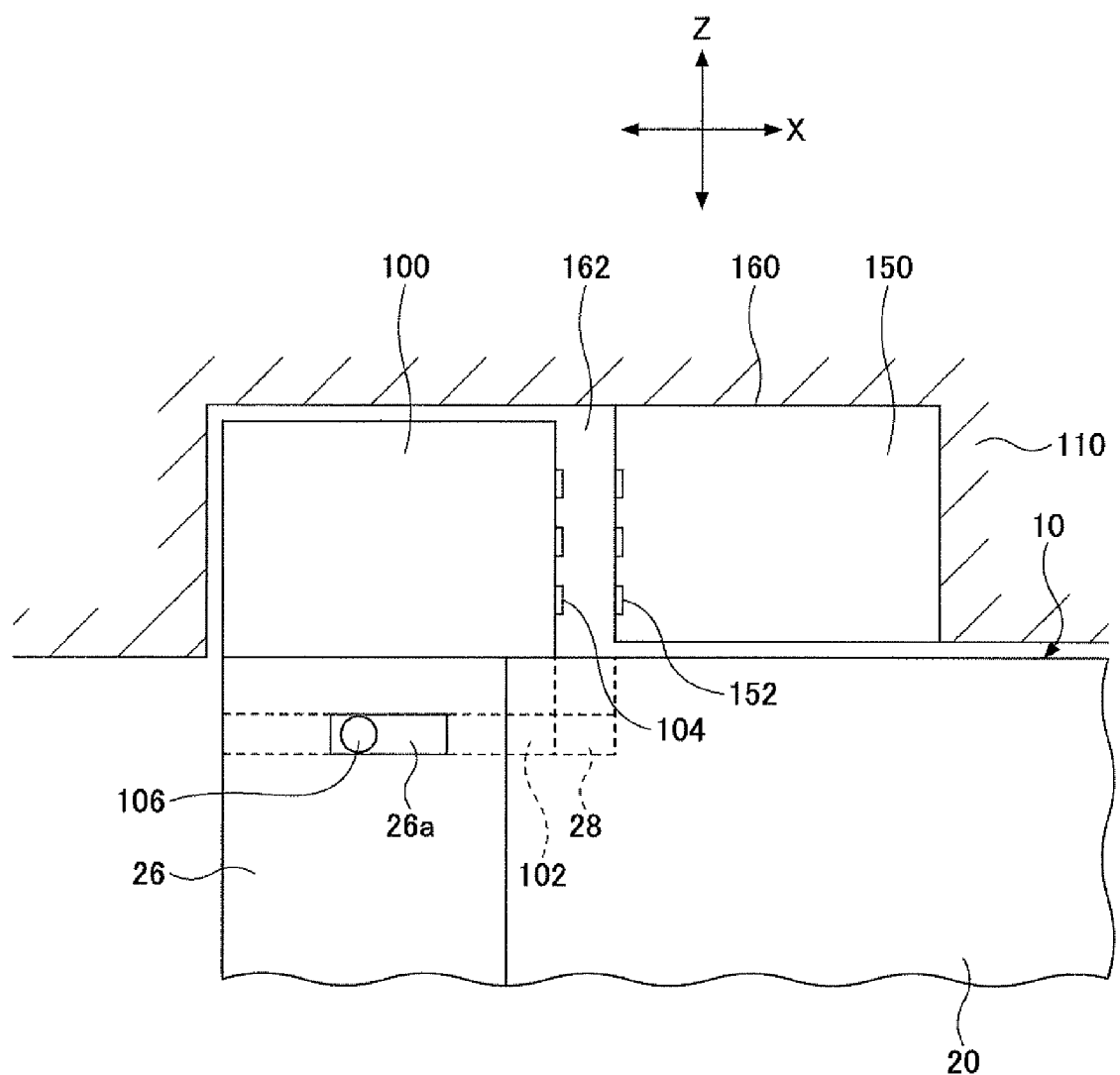
FIG. 4A is an enlarged view of a connector member at the upper end of the communication wall panel according to the embodiment of the present invention.
Figure 4B:
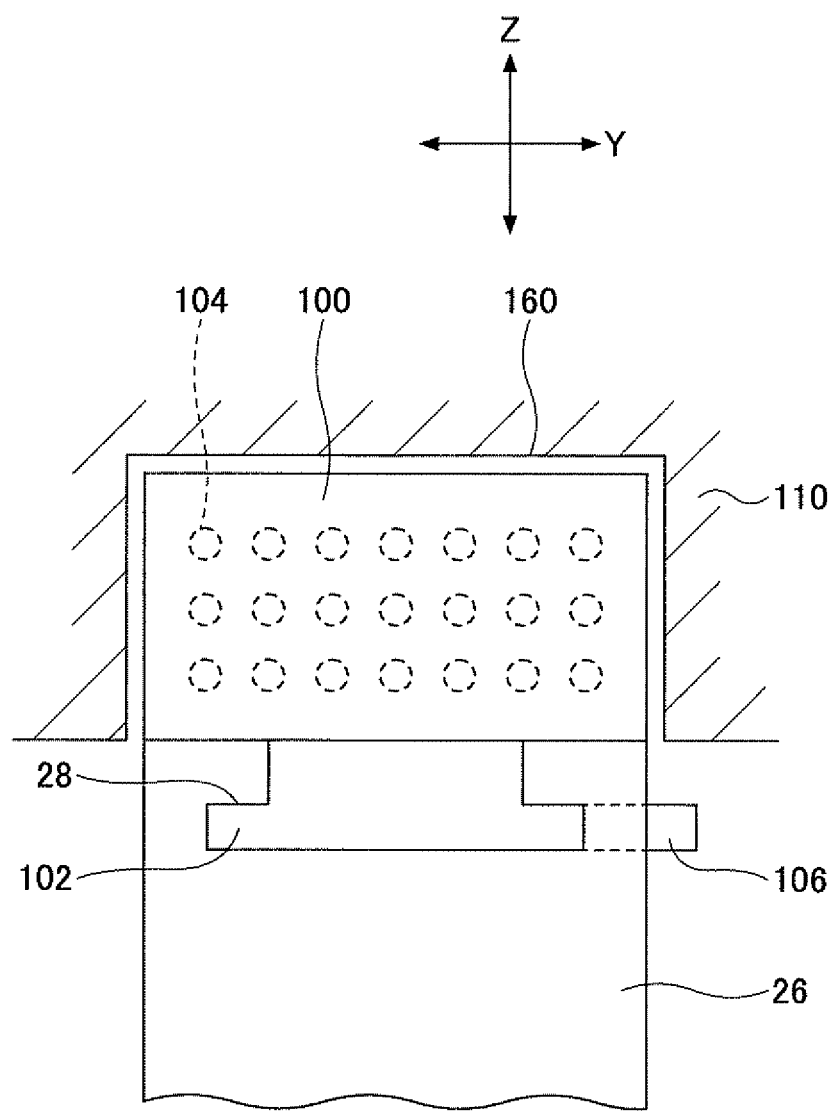
FIG. 4B is an enlarged side view of the connector member in its attached state according to the embodiment of the present invention.
Figure 4C:
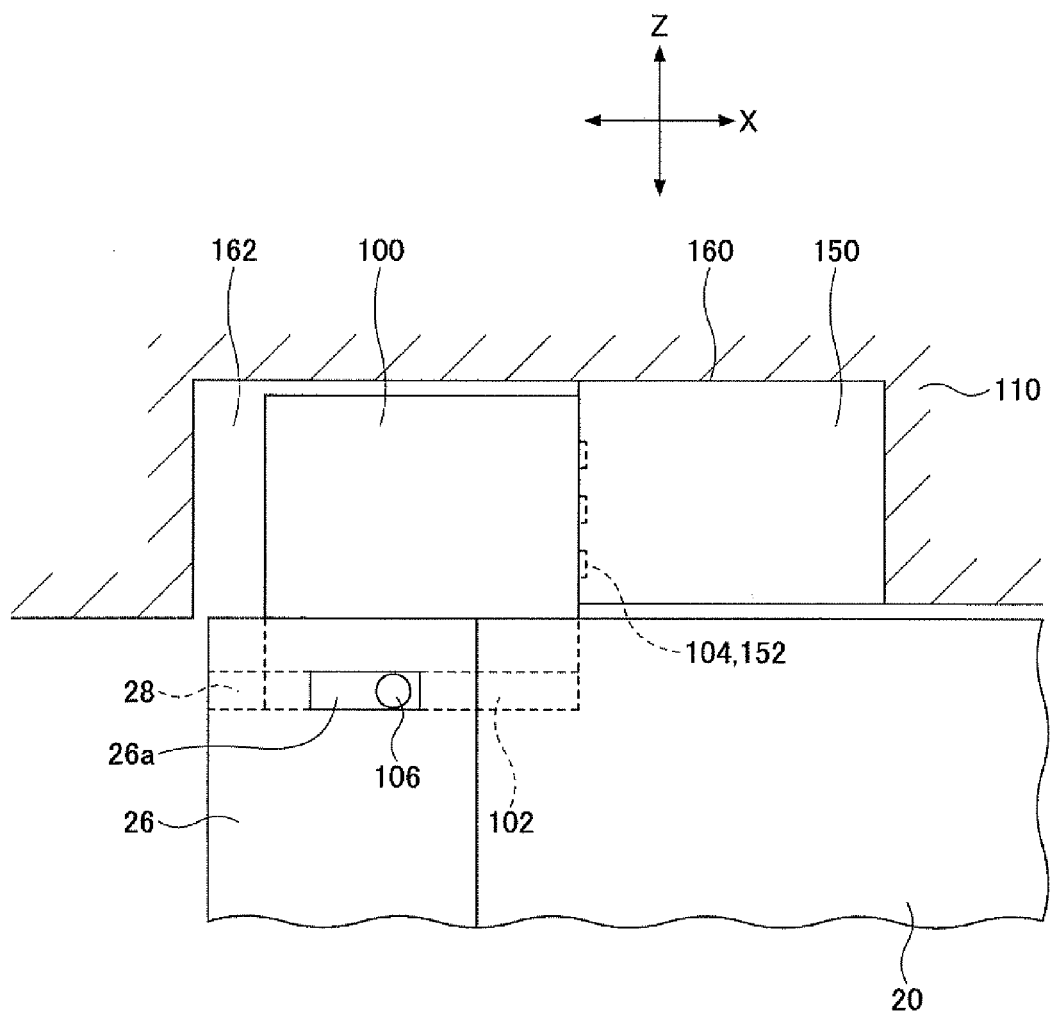
FIG. 4C is an enlarged view of the connector member in its connected state according to the embodiment of the present invention.

FIG. 4A is an enlarged view of the connector member 100 at the upper end of the communication wall panel 10. FIG. 4B is an enlarged side view of the connector member 100 in its attached state. FIG. 4C is an enlarged view of the connector member 100 in its connected state.

As illustrated in FIGS. 4A and 4B, the connector member 100 includes a flange part 102 at its lower end. The flange part 102 is fit into a guide groove 28 formed at the upper ends of the interconnection duct 26 and the interior panel member 20, so that the connector member 100 is attached to be movable horizontally (in the X directions). Further, multiple projecting contact parts 104 are provided on the right side face of the connector member 100 (FIG. 4A). Further, an operation knob 106 is provided on the front face of the flange part 102 of the connector member 100 through a front-side opening 26a of the interconnection duct 26. An electrical connection is established by sliding the operation knob 106 rightward in FIG. 4A.

A recess 160 to house the connector member 150 is formed in the ceiling 110 at a wall part 140 (FIG. 2) of the room to which the communication wall panel 10 is attached. An insertion part 162 into which the connector member 100 is inserted is formed in the recess 160. Multiple depressed contact parts 152 are formed on the left side face of the connector member 150 (FIG. 4A) to face the insertion part 162. Further, the insertion part 162 is formed to be larger in size than the connector member 100 having a parallelepiped shape. This allows the connector member 100 to be fit and housed smoothly.

The connector member 100 is covered with a metal cover member. Therefore, when the communication wall panel 10 is pressed, the connector member 100 comes into contact with the inner wall of the insertion part 162 to also operate as a stopper member to prevent a further movement of the communication wall panel 10.

When attaching the communication wall panel 10 to the wall face (wall part 140) of the room, the connector member 100 is inserted into the insertion part 162 of the recess 160 of the ceiling 110. As a result, the projecting contact parts 104 of the connector member 100 face the depressed contact parts 152 of the connector member 150.

Next, as illustrated in FIG. 4C, the operation knob 106 is pressed rightward to slide the connector member 100 toward the connector member 150 so that the projecting contact parts 104 are fit into and in contact with the corresponding depressed contact parts 152. By this simple operation of sliding the connector member 100 to the connector member 150, the connector members 100 and 150 are kept in an electrically connected state where the projecting contact parts 104 and the depressed contact parts 152 are electrically connected.

The operation of connecting the connector member 100 to the connector member 150 by pressing the operation knob 106 is performed with the communication wall panel 10 fixed to the ceiling 110 and the floor 120 in advance with the fixation mechanism 130.

The attachment position of the connector member 100 is not limited to the upper left end of the communication wall panel in its front view, and may be other positions.

Figure 5A:
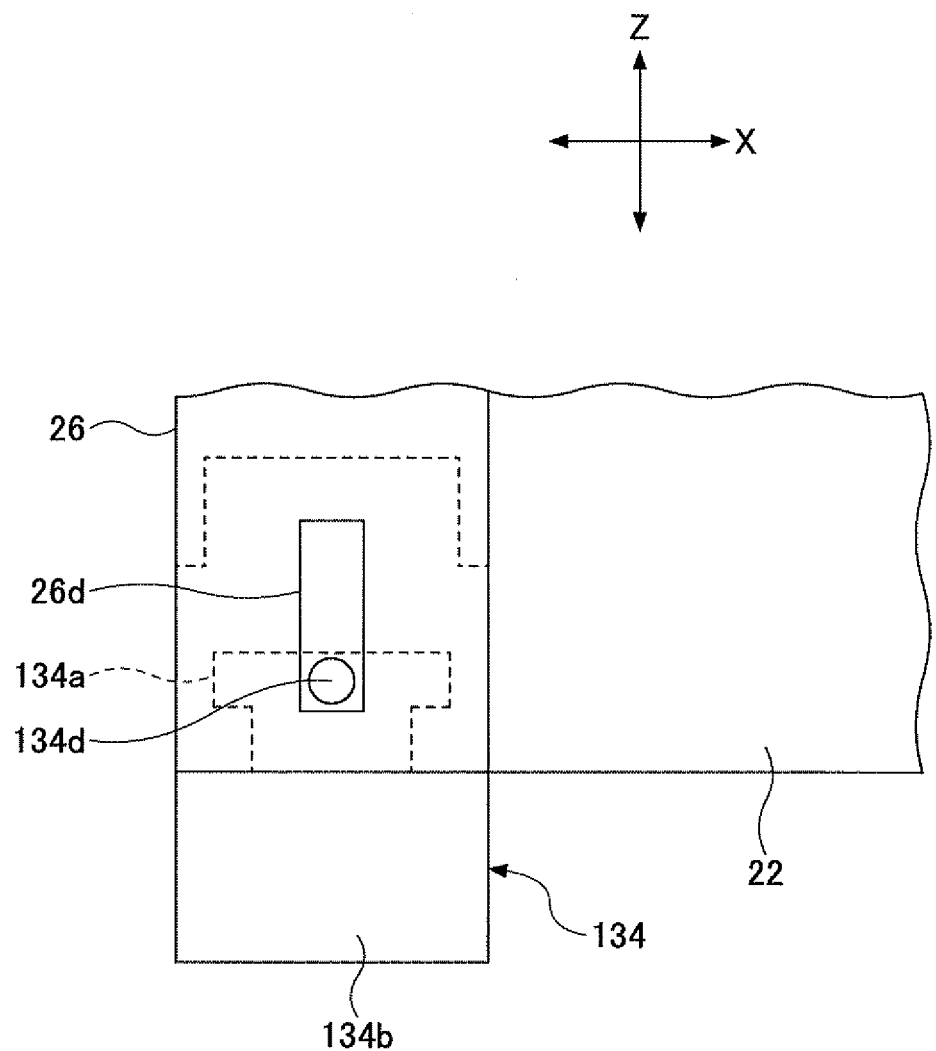
FIG. 5A is a front view of a fixation mechanism in its fixed state according to the embodiment of the present invention.
Figure 5B:
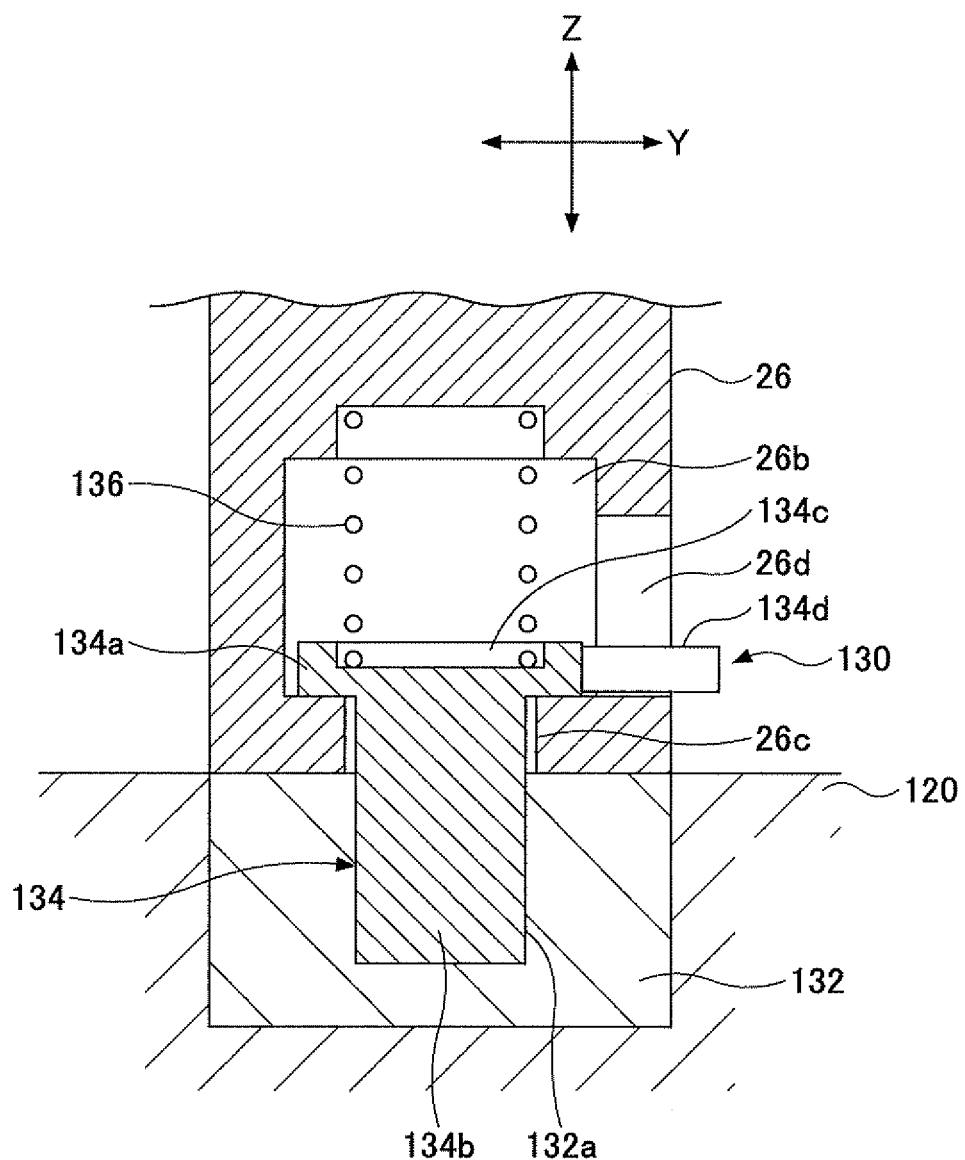
FIG. 5B is a cross-sectional view of the fixation mechanism in its fixed state according to the embodiment of the present invention.
Figure 5C:
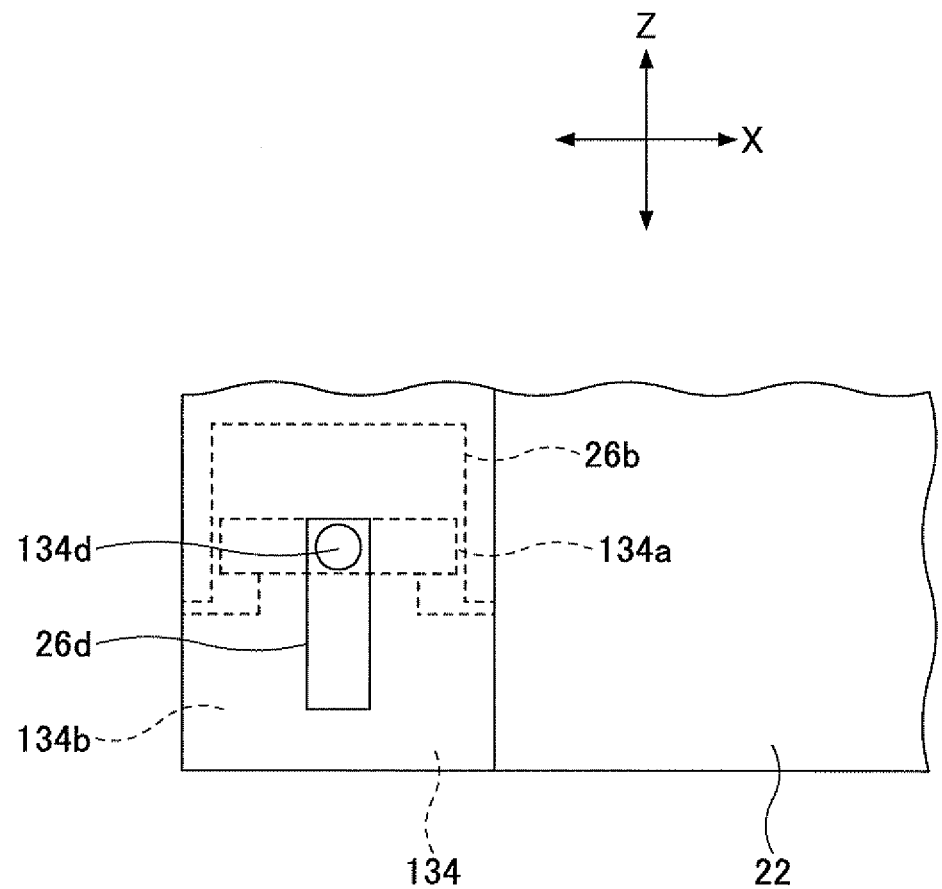
FIG. 5C is a front view of the fixation mechanism in its unfixed state according to the embodiment of the present invention.
Figure 5D:
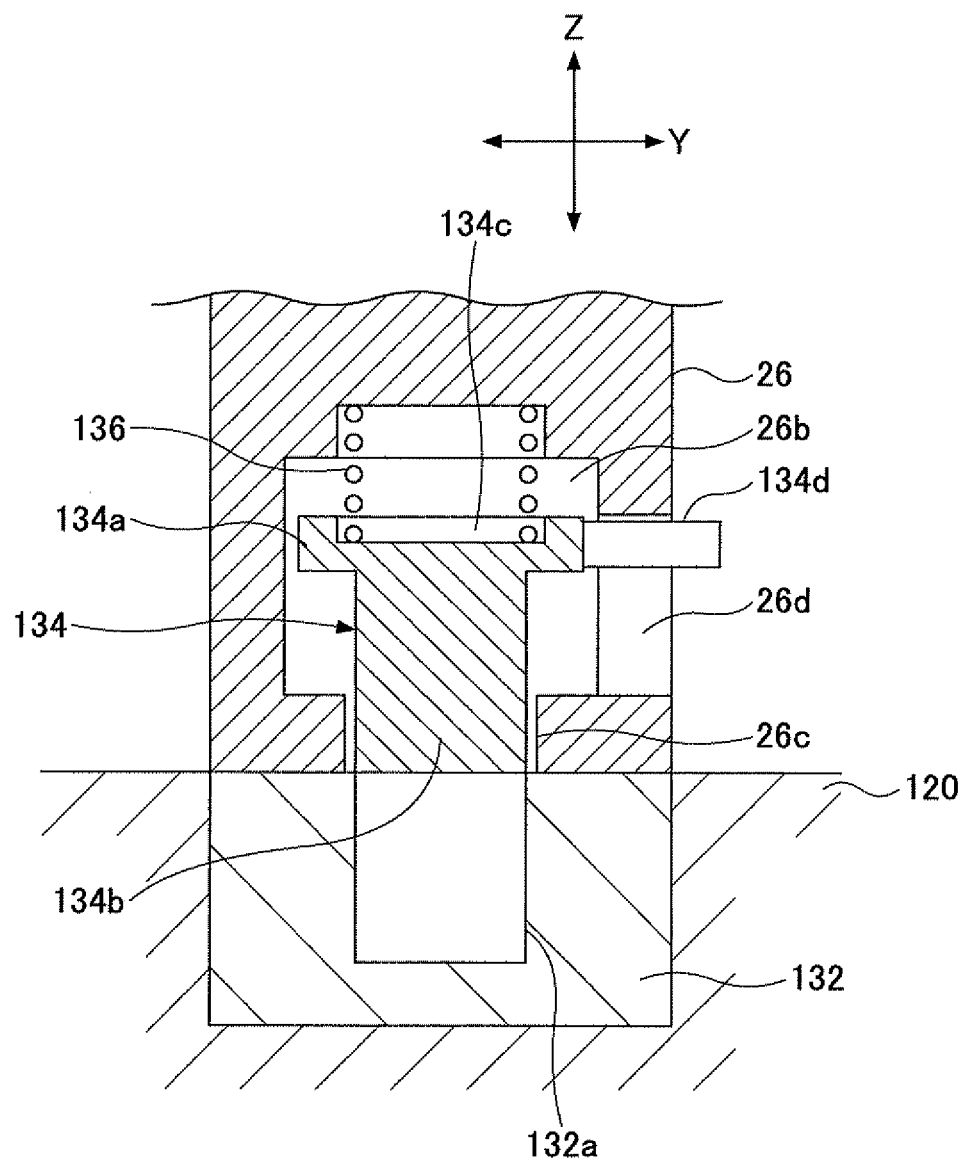
FIG. 5D is a cross-sectional view of the fixation mechanism in its unfixed state according to the embodiment of the present invention.

Here, a description is given of a configuration of the fixation mechanism 130. FIG. 5A is a front view of the fixation mechanism 130 in its fixed state at the lower end of the interconnection duct. FIG. 5B is a cross-sectional view of the fixation mechanism 130 in its fixed state at the lower end of the interconnection duct. FIG. 5C is a front view of the fixation mechanism 130 in its unfixed state at the lower end of the interconnection duct. FIG. 5D is a cross-sectional view of the fixation mechanism 130 in its unfixed state at the lower end of the interconnection duct.

As illustrated in FIGS. 5A and 5B, the fixation mechanism 130 includes the stopper member 134 to engage the engagement member 132 embedded in the floor 120 and an urging member 136 to urge the stopper member 134 toward a direction to fit the stopper member 134 into the engagement member 132. The stopper member 134 includes a sliding part 134a housed in a housing part 26b formed in a lower part of the interconnection duct 26, a fitting part 134b extending downward through a through hole 26c formed under the housing part 26b, a pressed part 134c formed at the upper end of the sliding part 134a and pressed by the urging member 136, and an operation knob 134d projecting in a sideward direction of the pressed part 134c (FIG. 5B, for example). Further, an insertion hole 26d through which the operation knob 134d is inserted is provided in a lower part of the front face of the interconnection duct 26.

As illustrated in FIGS. 5C and 5D, it is possible to disengage the stopper member 134 by moving it upward by pressing the operation knob 134d upward against the urging force of the urging member 136. That is, it is possible to remove restraint on the communication wall panel 10 by disengaging the fitting part 134b of the stopper member 134 from an engagement groove 132a of the engagement member 132 embedded in the floor 120.

Further, stopping pressing the operation knob 134d upward causes the stopper member 134 to slide downward because of the urging force of the urging member 136 so as to fit the fitting part 134 into the engagement groove 132a of the engagement member 132 embedded in the floor 120. As a result, the stopper member 134 has the fitting part 134b restrained by the engagement groove 132a of the engagement member 132, so that its horizontal movements are controlled to keep the communication wall panel 10 engaged with the floor 120.

The fixation mechanism 130 is also provided at the upper right end and the lower right end of the communication wall panel 10 in its front view (FIG. 1) in addition to the lower end of the interconnection duct 26. That is, the fixation mechanism 130 is provided at the corners of the communication wall panel 10 except where the connector member 100 is provided. Therefore, the communication wall panel 10 is fixed to the ceiling 110 and the floor 120 by sliding the stopper member 134 of the fixation mechanism 130 to an engagement position where the stopper member 134 engages the engagement groove 132a of the engagement member 132 at the three points.

Thus, moving the communication wall panel 10 may be facilitated by disengaging the stopper member 134 of the fixation mechanism 130 from the engagement groove 132a of the engagement member 132, and fixing the communication wall panel 10 to the ceiling 110 and the floor 120 may be facilitated by fitting the stopper member 134 of the fixation mechanism 130 into the engagement groove 132a of the engagement member 132.

The fixation mechanism 130 has a configuration similar to the configuration illustrated in FIGS. 5A through 5D at the upper right end and the lower right end of the communication wall panel 10 in its front view (FIG. 1).

Figure 6:
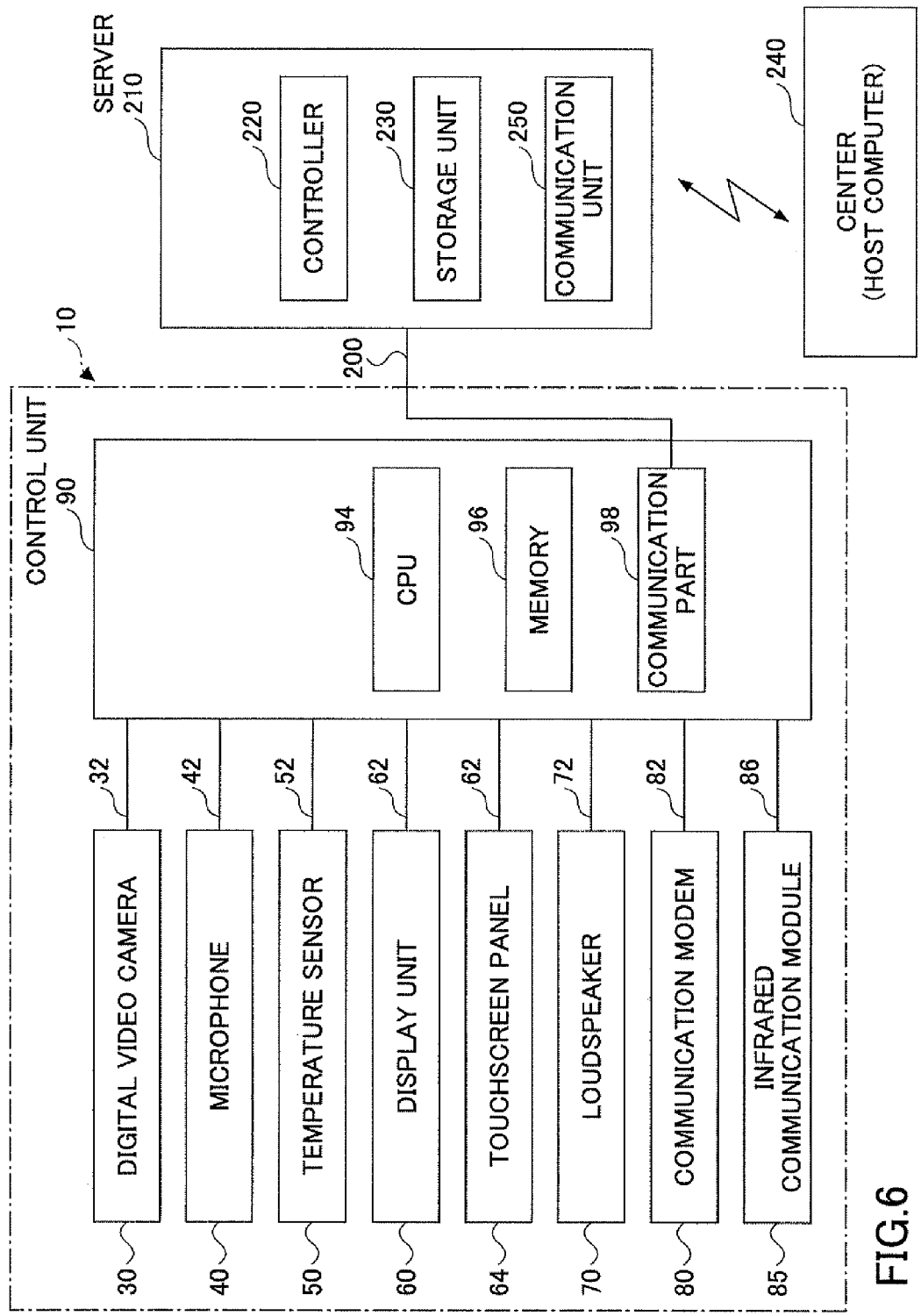
FIG. 6 is a block diagram illustrating a system configuration according to the embodiment of the present invention.

FIG. 6 is a block diagram illustrating a system configuration according to this embodiment. Referring to FIG. 6, a system according to this embodiment includes the communication wall panel 10 and a server 210. In the communication wall panel 10, the control unit 90 is connected to the digital video camera 30, the microphone 40, the temperature sensor 50, the display unit 60 including the touchscreen panel 64, the loudspeaker 70, the communication modem 80, and the infrared communication module 85 through the cables 32, 42, 52, 62, 72, 82, and 86, respectively. Further, the control unit 90 includes a communication part 98 to perform communications with the server 210. The communication part 98 includes, for example, a modem or a router. The communication part 98 is used to perform IP telephoning through the Internet or to conduct a videoconference with the outside.

The control unit 90 (the communication part 98) is connected to the server 210 in a communicable manner through the communication part 98 and a local area network (LAN) 200. The server 210 includes a controller 220 to transmit instructions to the control unit 90, a storage unit 230 including a hard disk unit to store information transmitted from the control unit 90, and a communication device 250 to communicate with the host computer of a center 240 through the Internet.

Control programs for various control modes executed by the control unit 90 may be prestored in the storage unit 230 of the server 210. Examples of such control modes include an IP telephone mode, a home appliance control mode, an image monitoring control mode using the digital video camera 30, a sound and vibration monitoring mode using the microphone 40, a room temperature and body temperature monitoring mode using the temperature sensor 50, a care control mode for managing the physical condition of a care recipient, and a videoconference control mode for videoconferencing with multiple persons.

When any control mode is selected and indicated by a voice input from the microphone 40 or a signal input from the touchscreen panel 64, the control unit 90 may download one of the control programs corresponding to the selected control mode from the storage unit 230 of the server 210, and the control unit 90 executes the selected control mode.

Figure 7:
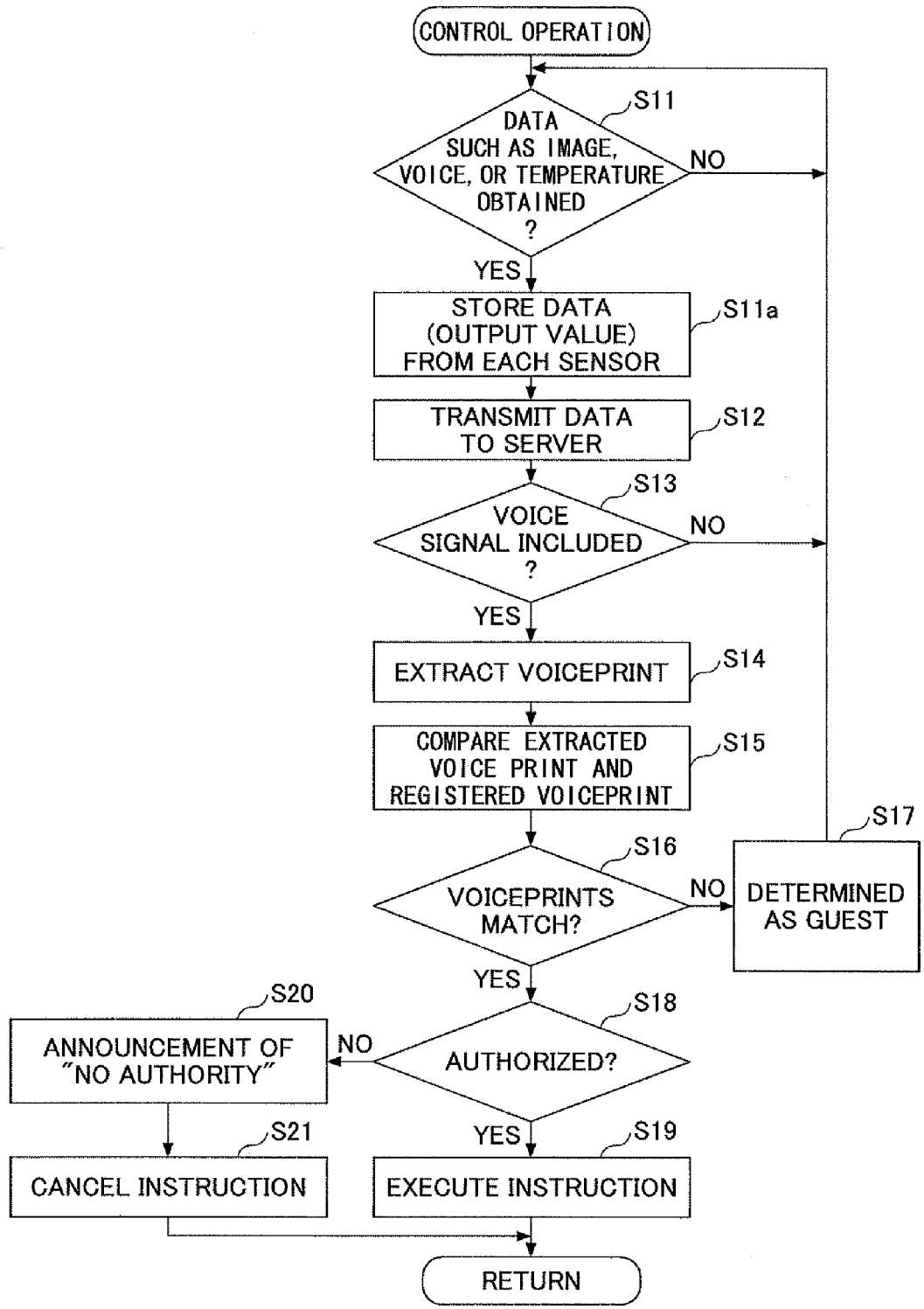
FIG. 7 is a flowchart for illustrating a control operation executed by a control unit according to the embodiment of the present invention.

Here, a description is given, with reference to the flowchart of FIG. 7, of a control operation executed by the control unit 90.

In step S11 of FIG. 7, the CPU 94 of the control unit 90 determines whether any of the signals from the digital video camera 30, the microphone 40, the temperature sensor 50, and the touchscreen panel 64 (for example, any of an image signal, an audio signal, a temperature detection signal, and an input signal) has been obtained (received). If any of the signals has been obtained (YES in step S11), the CPU 94 detects the presence of a person in the room, and determines that an activation signal for activating the system has been obtained to proceed to step S11a. In step S11a, the CPU 94 causes the output values (image signal, audio signal, temperature detection signal, and input signal) of the sensors (information obtaining parts such as the digital video camera 30, the microphone 40, the temperature sensor 50, and the touchscreen panel 64) to be stored in the memory 96 of the control unit 90 as detection data. Further, the output values (detection data) from the information obtaining part are stored in the memory 96 in time series. New data are stored in a predetermined storage area of the memory 96 while deleting data in order of expiration of the retention period. This data storage time (retention period) is set to a time corresponding to the storage capacity of the memory 96. Further, the data stored in the memory 96 are updated by overwriting older data with newer data, so that the output values for the past several seconds (for example, approximately five seconds to approximately ten seconds) are always retained temporarily.

Next, in step S12, the signals of the data (information) stored in the memory 96 are transmitted to the server 210. In the server 210, the transmitted data are stored in the large-capacity storage unit 230 including a hard disk unit.

Next, in step S13, it is determined whether a voice sound has been detected with the microphone 40 in the room where the communication wall panel 10 is installed. If a voice sound has been detected with the microphone 40 (YES in step S13), in step S14, the voiceprint data included in a voice signal indicating the detected voice sound, output by the microphone 40, are extracted. In step S15, the voiceprint data pre-registered with (pre-recorded in) the server 210 are read and compared with the voiceprint of the voice signal output by the microphone 40.

In step S16, it is determined whether the patterns of the voiceprints match. If the voiceprint of the voice signal output by the microphone 40 does not match the pre-registered voiceprint (NO in step S16), in step S17, it is determined that the voice is of a guest (someone from the outside). On the other hand, if the voiceprint of the voice signal output by the microphone 40 matches the pre-registered voiceprint (YES in step S16), the registered person (whose voiceprint has been registered) is identified (authenticated), and the operation proceeds to step S18.

In step S18, it is determined whether the registered person is authorized to instruct the control unit 90. If the registered person is authorized to instruct the control unit 90 (YES in step S18), in step S19, a voice instruction (such as an instruction to make a phone call or an instruction to change the set temperature of the air conditioner) is executed (processed).

If the registered person is not authorized to instruct the control unit 90 (NO in step S18), in step S20, a replay such as "YOU ARE NOT AUTHORIZED" is made through the loudspeaker. Then, in step S21, the voice instruction is canceled. Thus, it is possible to determine the presence of a person in the room by obtaining (receiving) at least one of the signals from the digital video camera 30, the microphone 40, the temperature sensor 50, and the touchscreen panel 64. Further, it is possible to identify (authenticate) a registered person and to determine whether the registered person has authority by comparing voiceprint data with her/his registered data. Accordingly, it is possible to determine the validity of a voice instruction with certainty.

Figure 8:
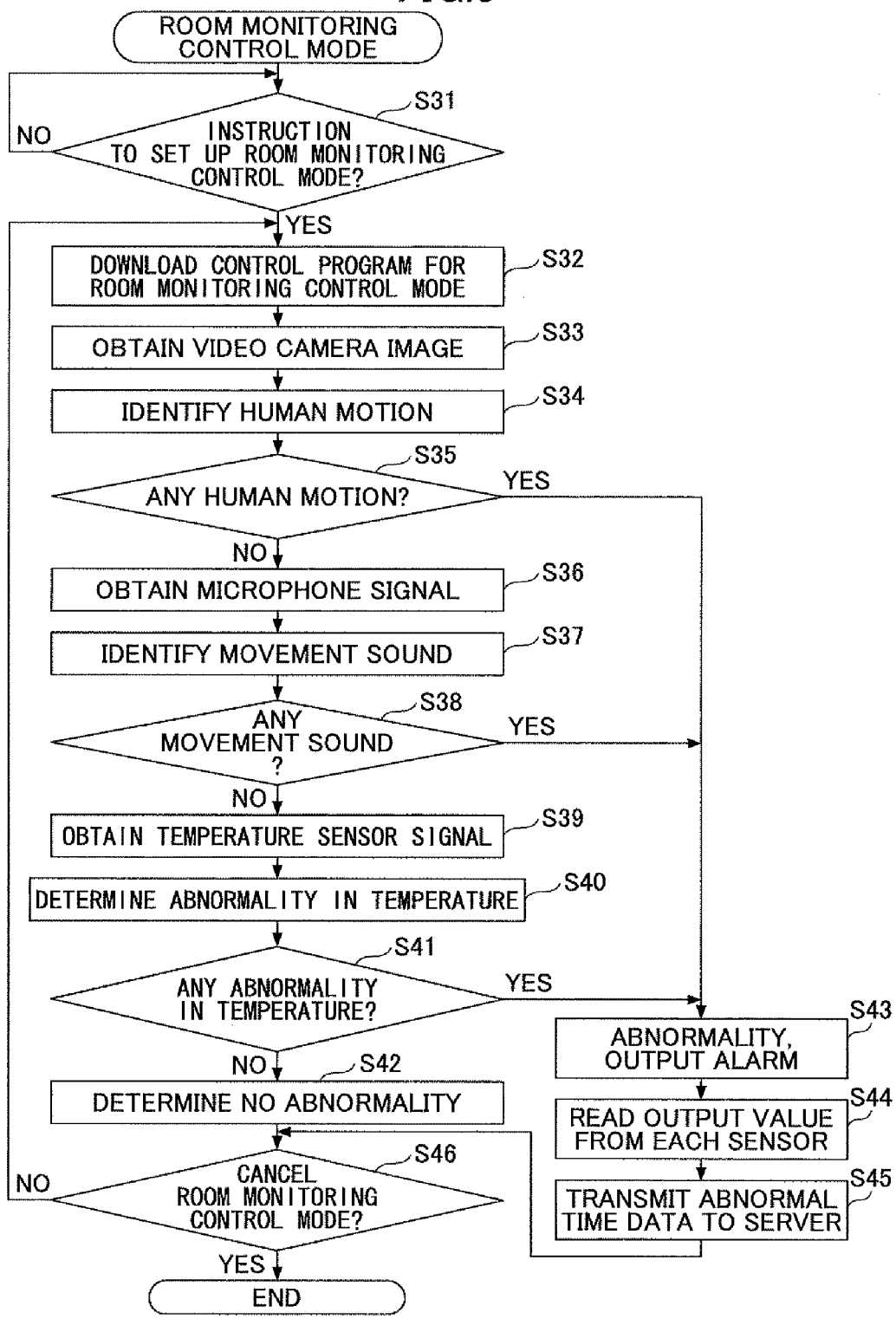
FIG. 8 is a flowchart for illustrating a control operation in the case where an instruction has been given to execute a room monitoring control mode according to the embodiment of the present invention.

Next, a description is given, with reference to the flowchart of FIG. 8, of a control operation in the case where an operator has given an instruction to execute the room monitoring control mode and the instruction is executed in step S19 of FIG. 7. This room monitoring control mode may be a security mode for confirming security that is set up when the operator goes out. For example, the room monitoring control mode may be a control mode for watching for an intruder or determining the presence or absence of an abnormality such as fire during the operator's absence.

In step S31 of FIG. 8, the CPU 94 of the control unit 90 determines whether an instruction to set up the room monitoring control mode has been given. If, for example, a voice instruction to set up the room monitoring control mode has been given (YES in step S31), in step S32, a control program for the room monitoring control mode is loaded by, for example, being downloaded from the server 210. Once the downloading of the control program for the room monitoring control mode is completed, the room monitoring control mode is entered after determining that the operator has gone out (in response to, for example, detecting the sound of closing and locking a door with the microphone 40, detecting no change in the temperature distribution for a predetermined period of time with the temperature sensor 50, or obtaining no image of a person from the room with the digital video camera 30).

In step S33, an image (video) of the room captured with the digital video camera 30 during a predetermined period of time (for example, 10 seconds) is obtained (received). In step S34, an operation is performed to identify (detect) a human motion from the room image. In step S35, it is determined whether there is a human motion. If there is a human motion in the room during the operator's absence (YES in step S35), in step S43, it is determined that there is an abnormality, and a voice alarm is output through the loudspeaker 70 and an abnormality occurrence signal is output to the server 210.

If there is no human motion in the room during the operator's absence (NO in step S35), in step S36, a voice signal indicating the voice detected with the microphone 40 during a predetermined period of time (for example, 10 seconds) is obtained (received). Then, in step S37, an operation is performed to identify (detect) a movement sound included in the sound signal output by the microphone 40. This movement sound is a man-made sound other than ordinary movement sounds (such as the sound of a clock and the sound of a telephone).

In step S38, it is determined whether an extraordinary movement sound has been detected. If an extraordinary movement sound has been detected (YES in step S38), in step S43, it is determined that there is an abnormality, and a voice alarm is output through the loudspeaker 70 and an abnormality occurrence signal is output to the server 210.

If no extraordinary movement sound has been detected (NO in step S38), in step S39, a temperature detection signal indicating the temperature detected with the temperature sensor 50 is obtained (received). In step S40, the presence or absence of an abnormal temperature (for example, a temperature higher than or equal to 50° C.) is determined from the temperature distribution in the room indicated by the temperature detection signal output by the temperature sensor 50.

Next, in step S41, it is determined whether an abnormal temperature has been detected from the room temperature distribution. If no abnormal temperature has been detected from the room temperature distribution (NO in step S41), in step S42, it is determined that there is no abnormality, and a signal indicating no abnormality is output to the server 210. If an abnormal temperature has been detected from the room temperature distribution (YES in step S41), in step S43, it is determined that there is an abnormality, and a voice alarm is output through the loudspeaker 70 and an abnormality occurrence signal is output to the server 210.

Further, in step S44, when each abnormality occurrence signal is output, the output value (image signal, audio signal, or temperature detection signal) obtained from a corresponding sensor (a corresponding information obtaining part such as the digital video camera 30, the microphone 40, or the temperature sensor 50), stored in the memory 96 for a predetermined period of time (any preset time) before and after the outputting of the abnormality occurrence signal, is read. Then, in step S45, the output value (detection data) read from the memory 96 in step S44 is output to the server 210 as abnormal time data. The server 210 stores the received abnormal time data in the storage unit 230, and further continues to store the latest output values from the sensors (information obtaining parts) (directly or through temporary storage in the memory 96) in the storage unit 230.

Thus, storing the output values obtained from information obtaining parts such as the digital video camera 30, the microphone 40, and the temperature sensor 50 for a predetermined period of time before and after the outputting of the corresponding abnormality occurrence signals makes it possible to investigate the condition of the room at the time of the outputting of the abnormality occurrence signals.

In step S46, it is determined whether an operation has been performed to cancel the room monitoring control mode. If the operator is not back home, it is impossible to give an instruction to cancel the room monitoring control mode (NO in step S46), so that the operation is repeated from step S32. On the other hand, if the operator comes home and gives an instruction to cancel the room monitoring control mode (YES in step S46), the room monitoring control mode is canceled, and the operation of the room monitoring control mode ends.

If an abnormality occurrence signal is output to the server 210 as described above, the abnormality occurrence signal is forwarded to the host computer of the center 240, and the center 240 reports the occurrence of the abnormality to a security company, the police, and/or a fire department. In response to this, security guards of the security company, police officers, and/or firefighters are called out and rush to the room whether the abnormality has occurred.

Figure 9:
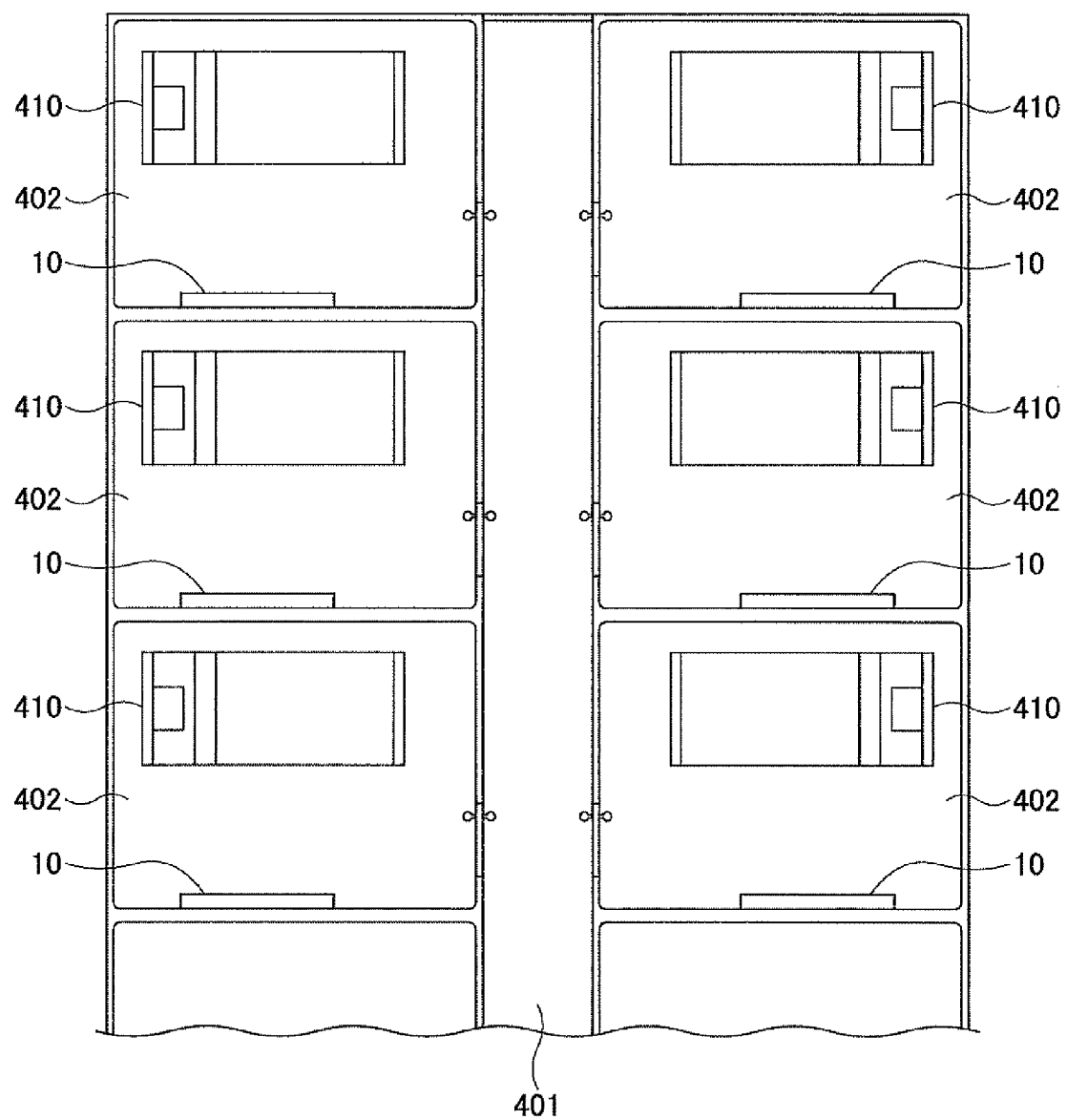
FIG. 9 is a schematic plan view of a care facility according to the embodiment of the present invention.

Next, a description is given of a nursing care system in the case of providing each room of a care facility with the communication wall panel 10 according to this embodiment. FIG. 9 is a schematic plan view of a care facility according to this embodiment.

Referring to FIG. 9, a care facility 400 includes multiple rooms 402 arranged side by side on each side of a hall 401. It is often the case that care recipients who receive care in the care facility 400 lie in respective care beds 410 installed in their rooms 402. Therefore, it is preferable to provide the communication wall panel 10 on a wall face near the care bed 410 in each room 402.

In the case of causing a care recipient to move, the care recipient moves from her/his room 402 through the hall 401 using a wheelchair in most cases. In the case of using the communication wall panel 10 for nursing care, it is possible to provide the digital video camera 30, the microphone 40, the temperature sensor 50, the display unit 60, the touchscreen panel 64, the loudspeaker 70, the communication modem 80, the infrared communication module 85, and the control unit 90 in each room 402 in a single operation by fixing the communication wall panel 10 to a wall face instead of providing them individually. This allows each room 402 to be spacious in use. Particularly, in the case of moving a wheelchair, such things as to hinder its passage cannot be placed around the care bed 410. Therefore, it is possible to reserve a passage space for the wheelchair by saving space by installing the communication wall panel 10.

Further, in the case of a care facility with a large number of rooms, it takes a lot of time and effort to install apparatuses individually. However, according to the method of installing the communication wall panel 10 on a wall face according to this embodiment, it is possible to substantially simplify installation operation, and it is also possible to reduce the work period of installation.

Figure 10:
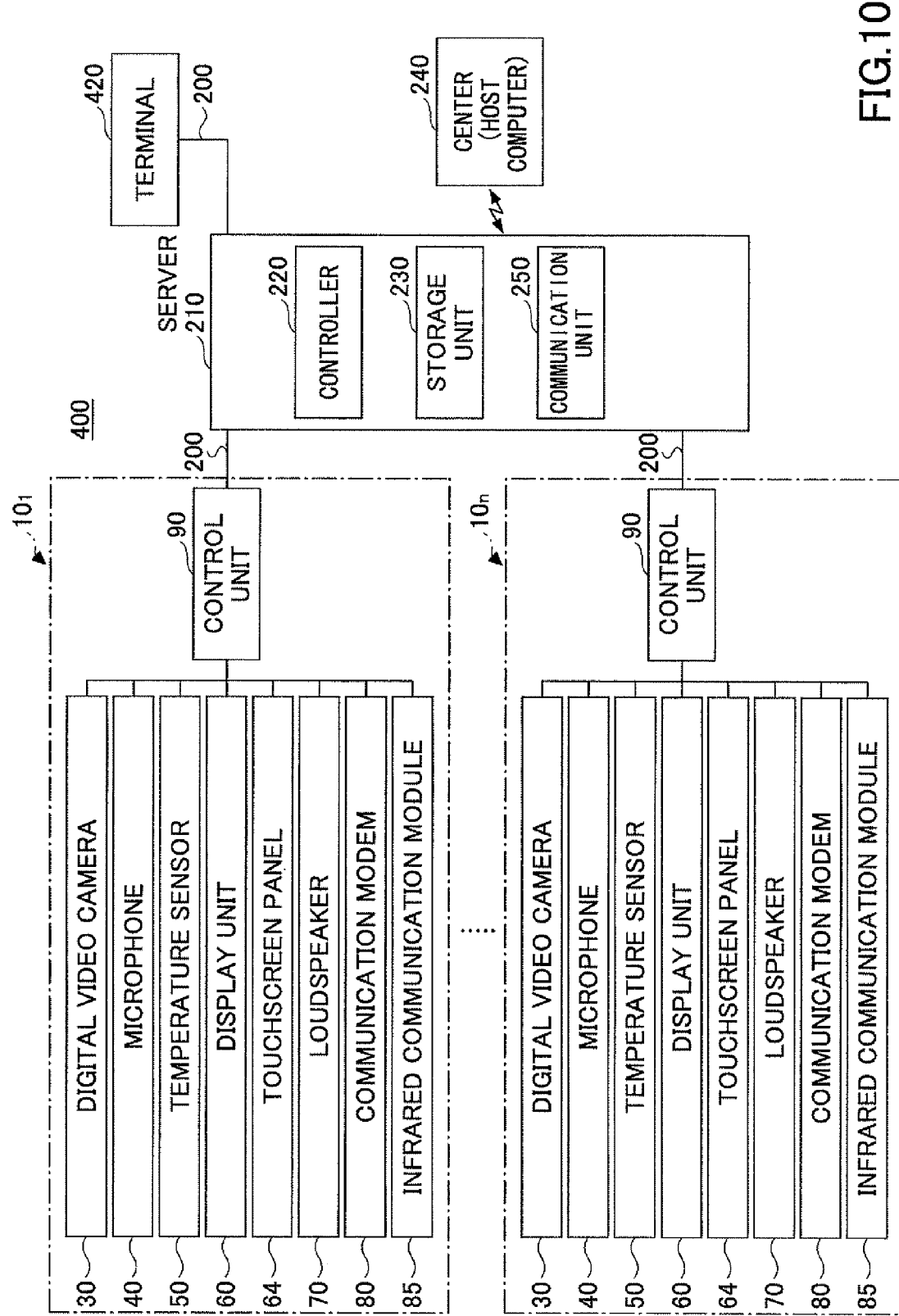
FIG. 10 is a block diagram illustrating a system configuration in the case of installing multiple communication wall panels in the care facility according to the embodiment of the present invention.

FIG. 10 is a block diagram illustrating a system configuration in the case of installing multiple communication wall panels 10 in a care facility. In FIG. 10, the same elements as those described above are referred to by the same reference numerals except that the communication wall panels 10 are referred to by reference numerals $10_1$ through $10_n$. Referring to FIG. 10, the communication wall panels $10_1$ through $10_n$ are connected through the LANs 200 to the server 210 installed in a nursing station. Further, the server 210 is connected to the host computer of the center 240 through the Internet in a communicable manner. The control unit 90 of each of the communication wall panels $10_1$ through $10_n$ constantly monitors the condition of the care recipient of the corresponding room 402, and transmits data obtained (received) from the digital video camera 30, the microphone 40, and the temperature sensor 50 serving as information obtaining parts to the server 210. This allows care workers to check the conditions of the care recipients of the rooms 402 by operating a terminal (such as a personal computer) 420 connected to the server 210.

Figure 11A:
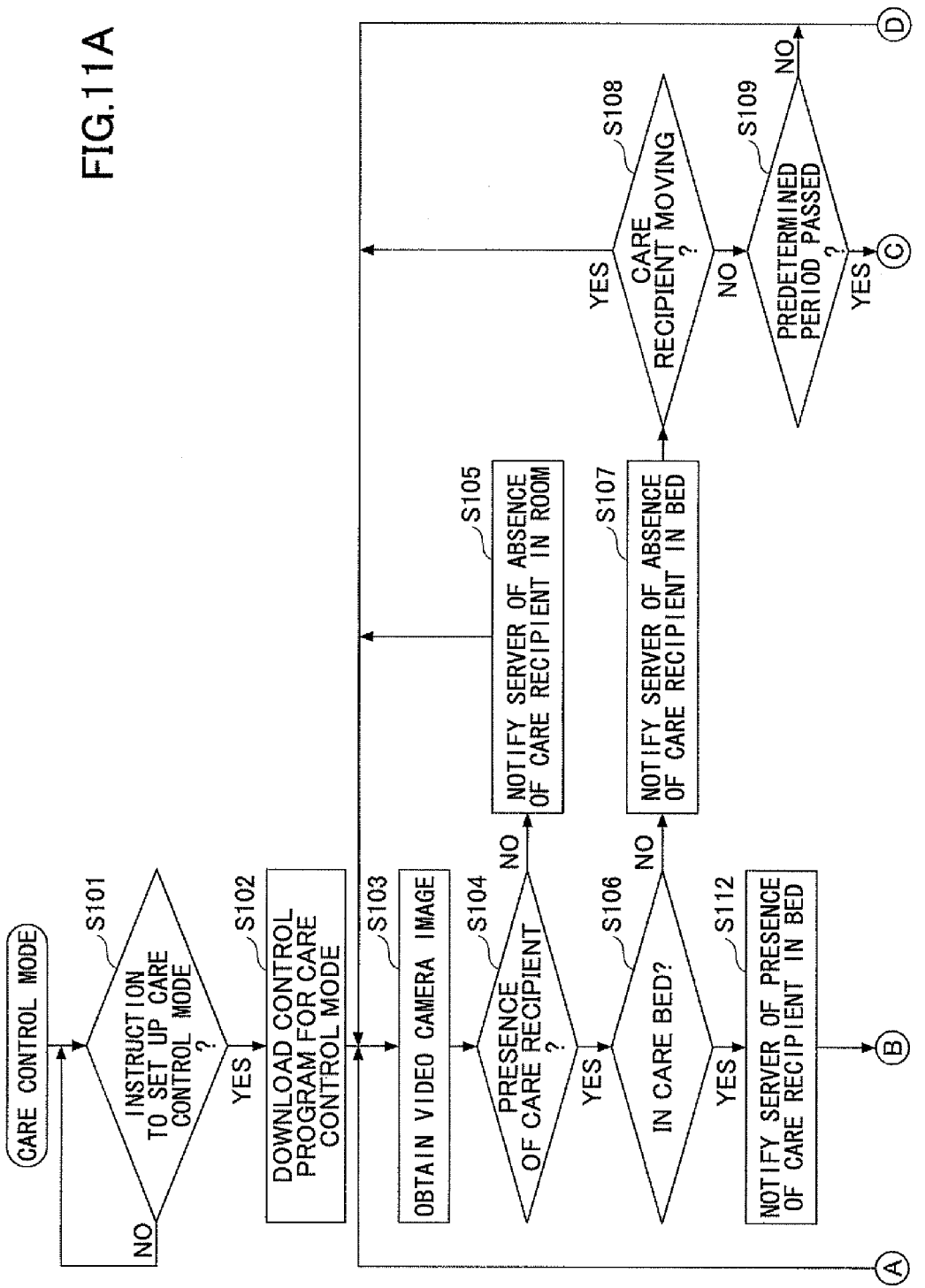
FIG. 11A is a flowchart for illustrating a control operation of a care control mode executed by a CPU of each of the control units of the communication wall panels according to the embodiment of the present invention.
Figure 11B:
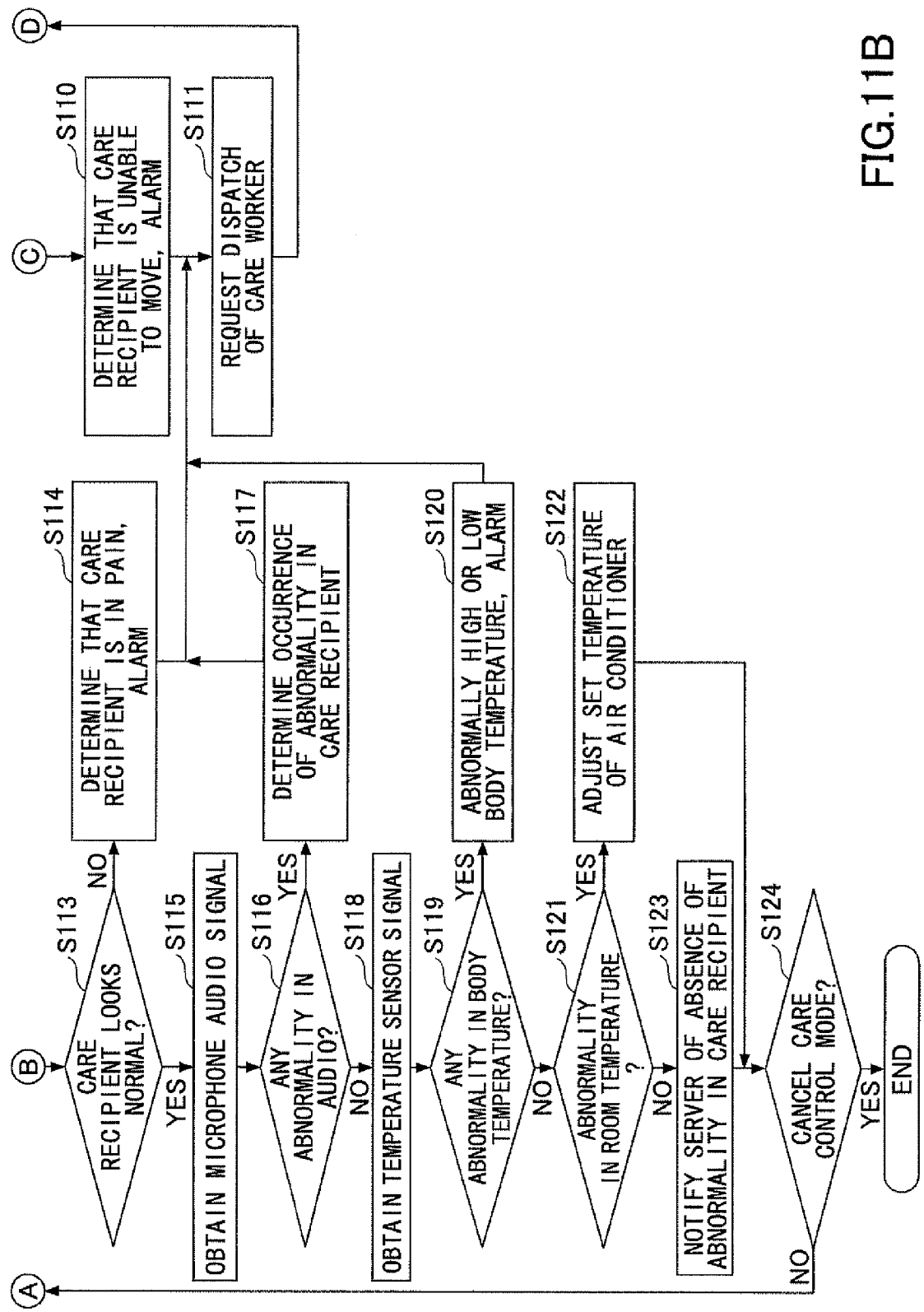
FIG. 11B is another flowchart for illustrating the control operation of the care control mode executed by the CUP of each of the control units of the communication wall panels according to the embodiment of the present invention.

Here, a description is given, with reference to the flowcharts of FIGS. 11A and 11B, of a control operation of the care control mode executed by the CPU 94 (FIG. 6) of each of the control units 90 of the communication wall panels $10_1$ through $10_n$.

In step S101 of FIG. 11A, the CPU 94 of the control unit 90 determines whether an instruction to set up the care control mode has been given. If, for example, a voice instruction to set up the care control mode has been given (YES in step S101), in step S102, a control program for the care control mode is loaded by, for example, being downloaded from the server 210. Once the downloading of the control program for the care control mode is completed, the care control mode is entered.

In step S103, an image (video) of the room 402 captured with the digital video camera 30 during a predetermined period of time (for example, 10 seconds) is obtained (received). Next, in step S104, it is determined from the image of the room 402 captured with the digital video camera 30 whether the care recipient is present. If the presence of the care recipient is not determined (NO in step S104), in step S105, the server 210 is notified of the absence of the care recipient in the room 402. Thereafter, the operation returns to step S103, and the operation is performed from step S103.

If the presence of the care recipient is determined from the image of the room 402 captured with the digital video camera 30 (YES in step S104), in step S106, it is determined whether the care recipient is in the care bed 410. If the care recipient is not in the care bed 410 (NO in step S106), in step S107, the server 210 is notified of the absence of the care recipient from the care bed 410.

Next, in step S108, it is determined whether the care recipient is moving in the room 402. If the care recipient is moving in the room 402 (YES in step S108), the operation returns to step S103, and the operation is performed from step S103. If the care recipient is stationary in the room 402 (NO in step S108), in step S109, it is determined whether a preset predetermined period of time (for example, 20 seconds) has passed.

If the predetermined period of time has not passed (NO in step S109), the operation returns to step S103, and the operation is performed from step S103. If the predetermined period of time has passed (YES in step S109), in step S110 of FIG. 11B, it is determined that the care recipient is unable to move in a place other than the care bed 410, and an alarm (warning) is output through the loudspeaker 70. Next, in step S111, an e-mail message requesting dispatch of a care worker is transmitted to the server 210. Thereafter, the operation returns to step S103, and the operation is performed from step S103.

Referring back to FIG. 11A, if the care recipient is in the care bed 410 (YES in step S106), in step S112, the server 210 is notified of the presence of the care recipient in the care bed 410. Then, in step S113 of FIG. 11B, it is determined from the image of the room 402 captured with the digital video camera 30 whether the care recipient looks normal. For example, if the care recipient is moving limbs violently, is in an unnatural position, or is having a pained expression on her/his face (NO in step S113), in step S114, it is determined that the care recipient is in pain in the care bed 410, and an alarm (warning) is output through the loudspeaker 70. Thereafter, in step S111, an e-mail message requesting dispatch of a care worker is transmitted to the server 210. Thereafter, the operation returns to step S103, and the operation is performed from step S103.

On the other hand, if the care recipient is stationary in the care bed 410 (YES in step S113), in step S115, a sound or vibration in the room 402 is detected with the microphone 40, and its audio signal is obtained (received). Next, in step S116, it is determined whether the obtained audio signal includes a signal indicating an abnormality. For example, if a painful voice of the care recipient, the care recipient's words asking for help, such a sound as is made by dropping an object onto a floor, or a sound like the cracking of an object is detected (YES in step S116), in step S117, it is determined that some abnormality has occurred with respect to the care recipient, and an alarm (warning) is output through the loudspeaker 70. Thereafter, in step S111, an e-mail message requesting dispatch of a care worker is transmitted to the server 210. Thereafter, the operation returns to step S103, and the operation is performed from step S103.

If the obtained audio signal includes no signal indicating an abnormality (NO in step S116), in step S118, a temperature detection signal indicating the temperature distribution of the room 402 detected with the temperature sensor 50 is obtained (received). Next, in step S119, it is determined whether the body temperature of the care recipient is an abnormal value. If the body temperature of the care recipient is high (for example, higher than or equal to 37° C.) or low (for example, lower than or equal to 36° C.) (YES in step S119), in step S120, it is determined that the body temperature is abnormal, and an alarm (warning) is output through the loudspeaker 70. Thereafter, in step S111, an e-mail message requesting dispatch of a care worker is transmitted to the server 210. Thereafter, the operation returns to step S103, and the operation is performed from step S103.

If the body temperature of the care recipient is not an abnormal value (for example, if the body temperature is higher than 36 and lower than 37° C.) (NO in step S119), in step S121, it is determined whether the room temperature is an abnormal value. For example, if the room temperature is lower than or equal to 22° C. or if the room temperature is higher than or equal to 28° C. (YES in step S121), it is determined that the room temperature is an abnormal value, and in step S122, an infrared signal for temperature control is caused to be transmitted from the infrared communication module 85 to the temperature control part of the air conditioner so as to adjust its set temperature.

If the room temperature is higher than 22° C. and lower than 28° C. (NO in step S121), it is determined that the room temperature is suitable, and in step S123, an e-mail message indicating the absence of an abnormality in the care recipient is transmitted to the server 210.

Next, in step S124, it is determined whether an instruction to cancel the care control mode has been input (received). If no instruction to cancel the care control mode has been input (NO in step S124), the operation returns to step S103, and the operation is performed from step S103. On the other hand, if a care worker has input an instruction to cancel the care control mode (YES in step S124), the care control mode is canceled and the operation of the care control mode ends. An instruction to cancel the care control mode may be given in the case of a care worker providing care, taking a care recipient to another room for medical examination, or taking a care recipient for a walk.

Thus, installing the communication wall panel 10 in each room 402 makes it possible to check the condition of the care recipient of each room 402, and also makes it possible to immediately view an e-mail message requesting dispatch of a care worker on the terminal 420 in the case of occurrence of any abnormality. This makes it possible to constantly monitor the conditions of multiple care recipients and allows a care worker to immediately help a care recipient in an abnormal condition.

Further, making the surface of the communication wall panel 10 (the interior panel member 20) equal in color to its surrounding wall allows a care recipient to be unaware of monitoring, thus making it possible to automatically report an abnormality without giving stress to the care recipient.

A description is given above of the control operation of the care control mode in the case of providing the multiple rooms 402 with their respective communication wall panels $10_1$ through $10_n$ in a care facility, while the present invention is also applicable to the case where care recipients receive home-visit nursing care while they are at home. In the case of home-visit nursing care, in each home, the communication wall panel 10 is installed in a room where a care bed is provided, and is connected in a communicable manner via a communication line such as a telephone line to the server 210 installed in a hospital or a care facility.

Next, a description is given of a videoconference system in the case of installing the communication wall panel 10 according to this embodiment in each of multiple offices.

Figure 12:
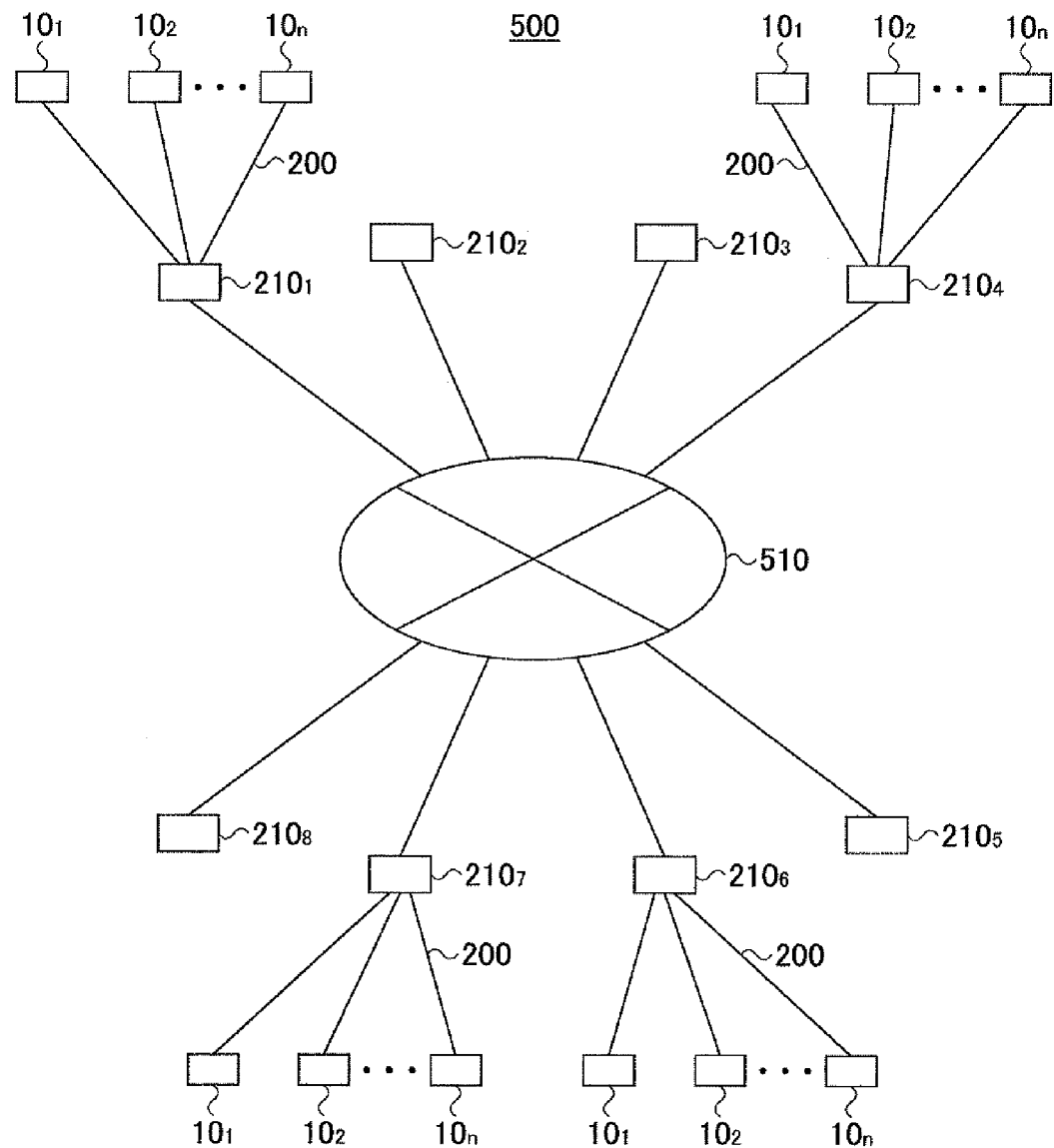
FIG. 12 is a schematic diagram illustrating a videoconference system according to the embodiment of the present invention.

FIG. 12 is a schematic diagram illustrating a videoconference system according to this embodiment.

Referring to FIG. 12, a videoconference system 500 includes the servers 210 (referred to by reference numerals $210_1$ through $210_8$ in FIG. 12) installed in respective business places and the communication wall panels $10_1$ through $10_n$ connected to each of the servers 210 ($210_1$ through $210_8$) through the corresponding LANs 200. The servers 210 ($210_1$ through $210_8$) are connected to the Internet 510 through communication devices such as routers.

Figure 13:
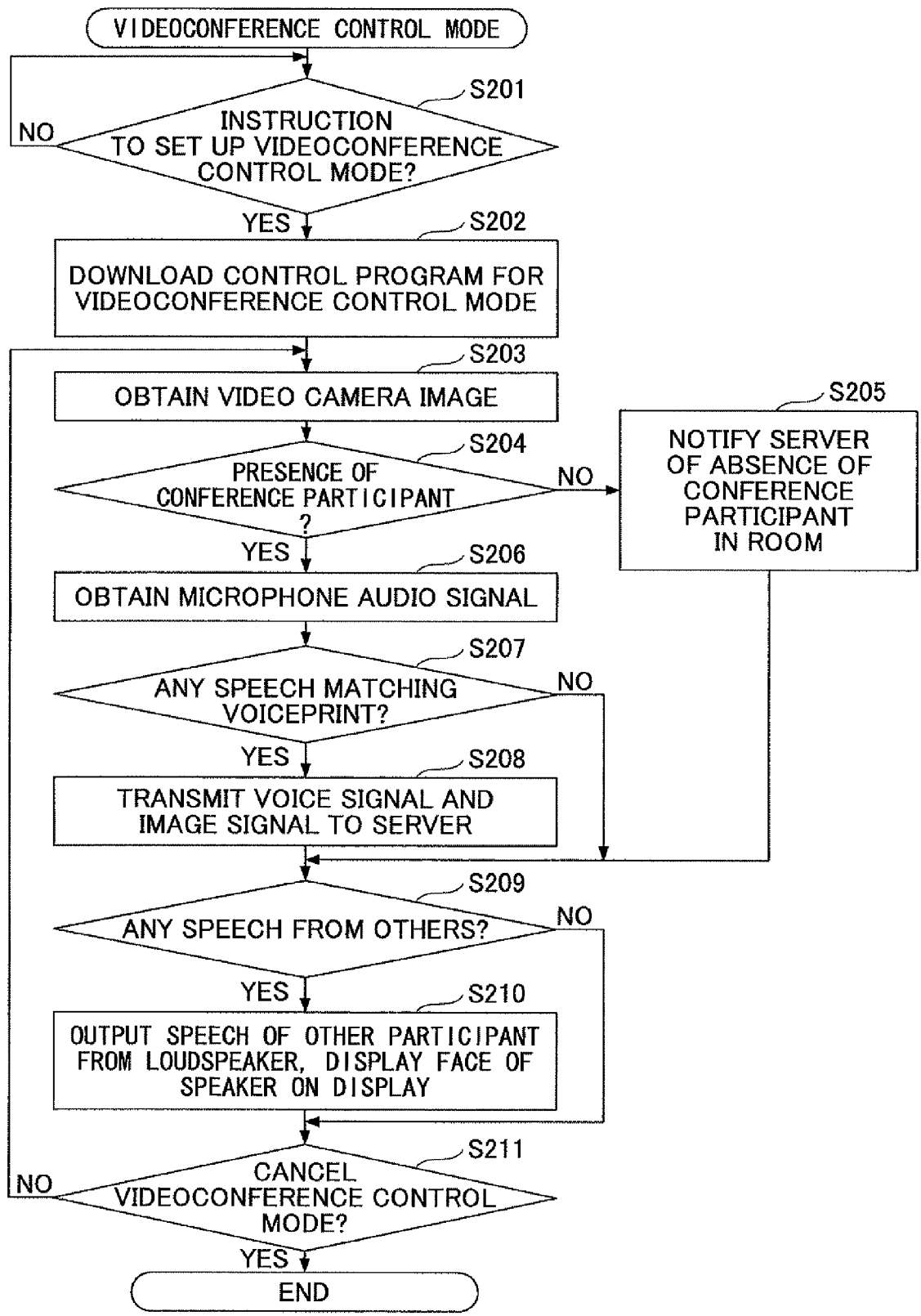
FIG. 13 is a flowchart for illustrating a control operation of a videoconference control mode executed by the CUP of each of the control units of the communication wall panels according to the embodiment of the present invention.

Here, a description is given, with reference to the flowchart of FIG. 13, of a control operation of the videoconference control mode executed by the CPU 94 (FIG. 6) of each of the control units 90 of the communication wall panels $10_1$ through $10_n$.

In step S201 of FIG. 13, the CPU 94 of the control unit 90 determines whether an instruction to set up the videoconference control mode has been given. If, for example, a voice instruction to set up the videoconference control mode has been given (YES in step S201), in step S202, a control program for the videoconference control mode is loaded by, for example, being downloaded from the server 210. Once the downloading of the control program for the videoconference control mode is completed, the videoconference control mode is entered.

In step S203, an image (video) of a room captured with the digital video camera 30 is obtained (received). Next, in step S204, it is determined from the image of the room captured with the digital video camera 30 whether a conference participant is present. If the presence of a conference participant is not determined (NO in step S204), in step S205, the server 210 is notified of the absence of a conference participant in the room. Thereafter, the operation proceeds to step S209 (described below), and steps S206 through S208 are omitted.

If the presence of a conference participant is determined from the image of the room captured with the digital video camera (YES in step S204), in step S206, a sound or vibration in the room is detected with the microphone 40, and its audio signal is obtained (received). Next, in step S207, it is determined whether the obtained audio signal includes speech of a voiceprint that matches the pre-registered voiceprint of the conference participant.

If the obtained audio signal includes speech of a voiceprint that matches the pre-registered voiceprint of the conference participant (YES in step S207), in step S208, the voice signal of the speech is extracted and transmitted to the server 210. Along with this, an image (video) of the room captured with the digital video camera 30 is transmitted to the server 210. If the obtained audio signal includes no speech MD in step S207), step S208 is omitted.

Next, in step S209, it is determined whether there is any speech from another conference participant. If there is speech from another conference participant (YES in step S209), in step S210, the face image of the speaker (the other conference participant) transmitted from the server 210 is displayed on the display unit 60 (FIG. 1), and the voice of the speaker is output from the loudspeaker 70. If there is no speech from any other conference participant (NO in step S209), step S210 is omitted.

Next, in step S211, it is determined whether an instruction to cancel the videoconference control mode has been input (received). If no instruction to cancel the videoconference control mode has been input (NO in step S211), the operation returns to step S203, and the operation is performed from step S203. If an instruction to cancel the videoconference control mode has been input (YES in step S211), the videoconference control mode ends.

In the server 210, a control operation is performed for distributing audio signals and image signals transmitted from its subordinate communication wall panels $10_1$ through $10_n$ to other communication wall panels $10_1$ through $10_n$.

Thus, compared with the case of providing videoconference facilities individually, installing the communication wall panels 10 on the wall faces of multiple offices saves time and effort in installation work, and requires less installation space to make it possible to make effective use of limited office space.

Further, the work for interconnecting apparatuses for a videoconference is simplified so that installation is performed with efficiency. Accordingly, even in the case of simultaneously installing the communication wall panels 10 in multiple offices at the time of introducing the videoconference system 500, it is possible to reduce a load (risk) at the introduction time by reducing working hours.

According to an aspect of the present invention, an information obtaining part, a notification part, a communication part, and a control part are provided in an interior panel member. Accordingly, it is possible to attach these apparatuses (parts) to a room in a single operation by attaching the interior panel member. This substantially reduces time and effort for installation work compared with the case of installing them individually, thus making it possible to perform installation with efficiency. Further, the work for interconnecting apparatuses is simplified, and it is possible to provide multiple cables without their exposure.

The present invention is not limited to the specifically disclosed embodiment, and variations and modifications may be made without departing from the scope of the present invention.

The present application is based on and claims the benefit of priority of Japanese Patent Application No. 2008-276738, filed on Oct. 28, 2008, the entire contents of which are incorporated herein by reference.

DESCRIPTION OF THE REFERENCE NUMERALS

10, $10_1$ through $10_n$ communication wall panel
20 interior panel member
24 interconnection groove
26 interconnection duct
30 digital video camera
32, 42, 52, 62, 72, 82, 86, 92 cable
40 microphone
50 temperature sensor
60 display unit
64 touchscreen panel
70 loudspeaker
80 communication modem
85 infrared communication module
90 control unit
94 CPU
96 memory
100 connector member
104 projecting contact part
106 operation knob
110 ceiling
120 floor
130 fixation mechanism
132 engagement member
134 stopper member
136 urging member
150 connector member
152 depressed contact part 160 recess
162 insertion part
210 server
220 controller
230 storage unit
240 center
250 communication device
400 care facility
402 room
410 care bed
420 terminal
500 videoconference system
510 Internet

The invention claimed is:

1. A communication wall panel, comprising:
an interior panel member to be attached to a room as an interior wall material thereof;
an information obtaining part provided in the interior panel member and configured to obtain information associated with a person in the room, the information obtaining part including a sound detection part configured to detect a sound in the room;
a notification part provided in the interior panel member and configured to notify the person in the room of information;
a communication part provided in the interior panel member and configured to perform communication with a server installed in a location other than the room; and
a control part provided in the interior panel member, the control part being configured to determine whether data of the sound detected by the sound detection part matches pre-registered data and to control the communication part and the notification part when determining that the data of the sound detected by the sound detection part matches the pre-registered data,
wherein the communication part is configured to transmit information obtained from the information obtaining part to the server and to output information transmitted from the server to the notification part.

2. The communication wall panel as claimed in claim 1, further comprising:
a connector member to be connected to a connector provided in the room, the connector member being provided on the interior panel member,
wherein the communication part is configured to be connected to the server in a communicable manner through the connector member and the connector.

3. The communication wall panel as claimed in claim 2, further comprising:
a plurality of cables connected to the connector member, the information obtaining part, the notification part, the communication part, and the control part, the cables being provided on a backside of the interior panel member.

4. The communication wall panel as claimed in claim 1, wherein the information obtaining part further comprises at least one of an image capturing part configured to capture a digital image of the room and a temperature detection part configured to detect a temperature in the room.

5. The communication wall panel as claimed in claim 1, wherein the notification part comprises at least one of a display unit configured to display image information transmitted from the server and a loudspeaker configured to output audio information transmitted from the server.

* * * * *